(12) United States Patent
Yachi et al.

(10) Patent No.: US 10,619,058 B2
(45) Date of Patent: *Apr. 14, 2020

(54) CURABLE COMPOSITION

(71) Applicant: TOAGOSEI CO., LTD., Tokyo (JP)

(72) Inventors: Kentaro Yachi, Nagoya (JP); Naoki Hashimoto, Nagoya (JP)

(73) Assignee: TOAGOSEI CO., LTD., Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 15/739,540

(22) PCT Filed: Jul. 1, 2016

(86) PCT No.: PCT/JP2016/069639
§ 371 (c)(1),
(2) Date: Dec. 22, 2017

(87) PCT Pub. No.: WO2017/002961
PCT Pub. Date: Jan. 5, 2017

(65) Prior Publication Data
US 2018/0187026 A1    Jul. 5, 2018

(30) Foreign Application Priority Data

Jul. 2, 2015 (JP) ................. 2015-133196

(51) Int. Cl.
| | | |
|---|---|---|
| C09D 5/44 | (2006.01) | |
| B01J 31/04 | (2006.01) | |
| C07C 67/03 | (2006.01) | |
| C08F 20/20 | (2006.01) | |
| C09D 11/101 | (2014.01) | |
| B01J 31/22 | (2006.01) | |
| C09D 4/00 | (2006.01) | |
| C07C 69/54 | (2006.01) | |
| B01J 23/06 | (2006.01) | |

(52) U.S. Cl.
CPC ............. C09D 5/4411 (2013.01); B01J 23/06 (2013.01); B01J 31/04 (2013.01); B01J 31/22 (2013.01); B01J 31/2239 (2013.01); C07C 67/03 (2013.01); C07C 69/54 (2013.01); C08F 20/20 (2013.01); C09D 4/00 (2013.01); C09D 11/101 (2013.01)

(58) Field of Classification Search
CPC ...... C09D 5/4411; C09D 11/101; B01J 31/04; B01J 31/22; B01J 31/2239; B01J 23/06; C07C 67/03; C07C 69/54; C08F 20/20
USPC ...................................... 526/323.1
See application file for complete search history.

(56) References Cited

U.S. PATENT DOCUMENTS

| | | |
|---|---|---|
| 2014/0198285 A1 | 7/2014 | Fujita et al. |
| 2017/0204044 A1 | 7/2017 | Hashimoto et al. |

FOREIGN PATENT DOCUMENTS

| | | | |
|---|---|---|---|
| JP | 53-105417 A | | 9/1978 |
| JP | S53105417 A | * | 9/1978 |
| JP | 2-279775 A | | 11/1990 |
| JP | 9-95517 A | | 4/1997 |
| JP | 2000-302997 A | | 10/2000 |
| JP | 2001-278924 A | | 10/2001 |
| JP | 2001-316328 A | | 11/2001 |
| JP | 2002-3444 A | | 1/2002 |
| JP | 2003-190819 A | | 7/2003 |
| JP | 2009-287017 A | | 12/2009 |
| JP | 2009287017 A | * | 12/2009 |
| JP | 2013-76926 A | | 4/2013 |
| JP | 2013-159615 A | | 8/2013 |
| JP | 2013159615 A | * | 8/2013 |
| JP | 2014084339 A | * | 5/2014 |
| WO | WO 2015/159611 A1 | | 10/2015 |

OTHER PUBLICATIONS

International Search Report for PCT/JP2016/069639 (PCT/ISA/210) dated Sep. 13, 2016.
Maegawa et al., "Additive Effect of N-Heteroaromatics on Transesterification Catalyzed by Tetranuclear Zinc Cluster", ACS Publications, 2011 American Chemical Society, vol. 1, No. 10, pp. 1178-1182.
Written Opinion of the International Searching Authority for PCT/JP2016/069639 (PCT/ISA/237) dated Sep. 13, 2016.
Chinese Office Action for corresponding Chinese Application No. 201680036266.9, dated Nov. 4, 2019, with a partial English translation.

* cited by examiner

Primary Examiner — Michael Bernshteyn
(74) Attorney, Agent, or Firm — Birch, Stewart, Kolasch & Birch, LLP

(57) ABSTRACT

A curable composition is provided that has low viscosity and rapid curing ability in the form of thin film, further has excellent resistance to emulsification and preservation stability, and has high hardness in the form of cured film, thereby achieving excellent alkali developability, which is preferably an active energy beam-curable composition. The curable composition includes a mixture (A) of a compound having two or more (meth)acryloyl groups that is obtained by conducting a transesterification reaction of a polyalcohol and a compound having one (meth)acryloyl group under the presence of catalysts X and Y. Catalyst X is a compound that is at least one of a cyclic tertiary amine having an azabicyclo structure or a salt or complex thereof, an amidine or a salt or complex thereof, and a compound having a pyridine ring or a salt or complex thereof. Catalyst Y is a compound including zinc.

7 Claims, No Drawings

CURABLE COMPOSITION

TECHNICAL FIELD

The present invention relates to a curable composition and preferably relates to an active energy beam-curable composition. The composition of the invention can be used for various purposes. In particular, the composition can be preferably used for coating agents for hard coating, etc., ink for offset or ink-jet printing, etc., pattern formation agents for photosensitive lithographic printing plates and color resists, etc. The composition of the invention belongs to these technical fields.

It is herein specified that the acryloyl group and/or the methacryloyl group is expressed as the (meth)acryloyl group, the acrylate and/or methacrylate is expressed as (meth)acrylate, and acrylic acid and/or methacrylic acid is expressed as (meth)acrylic acid.

BACKGROUND ART

As active energy beam-curable compositions, compositions including compounds having two or more (meth)acryloyl groups (hereinafter referred to as "polyfunctional (meth)acrylate") are used for various purposes. In particular, compositions including, as a main component, a mixture of dipentaerythritol pentaacrylate and dipentaerythritol hexaacrylate (hereinafter referred to as "DPHA") or a mixture of pentaerythritol triacrylate and pentaerythritol tetraacrylate (hereinafter referred to as "PETTA") are used for various purposes by making use of its excellent physical properties.

A cured film obtained from a composition including DPHA and/or PETTA is widely used for hard coating because such cured film has features of having high surface hardness and being resistant to scratches (Patent Document 1).

DPHA is highly viscous and PETTA is solid at ordinary temperature, which makes it difficult to conduct solventless formation of the composition. Patent Document 2 discloses an active energy beam-curable composition, which includes not less than 30 parts by weight of a compound having one (meth)acryloyl group (hereinafter referred to as "monofunctional (meth)acrylate") or a compound having two (meth) acryloyl groups (hereinafter referred to as "bifunctional (meth)acrylate"), in order to decrease the viscosity of DPHA.

However, the composition of Patent Document 2 is problematic in that hardness of a cured film formed on a plastic film is excessively low.

In addition, DPHA and PETTA are usually produced via dehydration esterification of a polyalcohol and acrylic acid. As these products contain a high-molecular-weight body, which is one cause of reduction of cured film hardness. There is a demand to improve cured film hardness.

Further, as DPHA is excellent in terms of surface curing ability, it is used for ink, and it is widely used especially as a resin composition for active energy beam-curable offset ink (Patent Document 3).

DPHA and PETTA are produced via dehydration esterification as described above. Therefore, these products contain a high-molecular-weight body, which might be one cause of reduction of emulsification stability.

Patent Document 4 discloses that after a step of removing unreacted acrylic acid, washing is performed with a mixture of a specific solvent and water so that a water-soluble component is removed, thereby making it possible to improve emulsification stability.

However, in this case, a waste solvent and a waste liquid increase. Therefore, instead of this method, a production method whereby a high-molecular-weight body can be reduced has been awaited.

Moreover, for the reason that a composition including DPHA or PETTA and an alkali-soluble resin has high sensitivity, the composition is widely used as a resin composition for active energy beam-curable pattern formation (Patent Document 5).

As described above, since DPHA or PETTA are produced via dehydration esterification, alkali metal ions derived from an alkali metal aqueous solution used in the step of removing unreacted acrylic acid remain at 1 ppm or more in a product. This might cause a problem of reduction of electric properties due to metal ion elution from a cured film.

Patent Document 6 discloses that elution of metal ions is reduced by improving adhesion between a substrate and a cured film, thereby achieving favorable specific resistance of liquid crystal when the composition is used for a liquid crystal display device.

However, performance of the composition is still insufficient, and therefore, there is a demand to radically reduce the amount of metal ions in DPHA or PETTA.

As stated above, if it is possible to obtain a compound containing, as a material polyfunctional (meth)acrylate, a high-molecular-weight body in a small amount for a composition including a polyfunctional (meth)acrylate, it is considered possible to solve the various problems described above.

As a method of producing (meth)acrylate for preventing generation of a high-molecular-weight body, a transesterification method using a tin catalyst or a titanium catalyst is known (Patent Documents 7 and 8).

In the conventional transesterification reaction, however, in a case in which a polyalcohol having three or more alcoholic hydroxyl groups is used as a starting material, the reaction rate is low even when the reaction is conducted for a long time, which results in a low ideal-structure (meth) acrylate concentration and a low level of cured film hardness. This has been problematic.

Meanwhile, a transesterification method using a phosphine-based catalyst is known, which is excellent in terms of catalyst activity as a method of producing a polyfunctional (meth)acrylate (Patent Document 9).

As a result of studies made by the present inventors, a phosphine-based catalyst present in a reaction solution after the termination of reaction is problematic in view of production because it is difficult to remove the catalyst from the reaction solution by a convenient method involving filtration and adsorption, etc. The phosphine-based catalyst remains even in a final product. This causes problems of preservation stability, such as turbidity or precipitation of the catalyst that appears during storage of a product or thickening or gelling that occurs over time. Also in a case in which the catalyst is used as a component of a composition, there have been similar problems.

PRIOR ART REFERENCES

Patent Documents

Patent Document 1: Japanese Patent Application Laid-Open (JP-A) No. 2001-278924
 Patent Document 2: JP-A No. 2009-287017
 Patent Document 3: JP-A No. 2000-302997

Patent Document 4: JP-A No. H02-279775
Patent Document 5: JP-A No. H09-95517
Patent Document 6: JP-A No. 2013-76926
Patent Document 7: JP-A No. 2003-190819
Patent Document 8: JP-A No. 2002-3444
Patent Document 9: JP-A No. 2001-316328

SUMMARY OF INVENTION

Problems to be Solved by the Invention

The inventors made intensive studies to find out a curable composition that has a low level of viscosity and rapid curing ability in the form of thin film, excellent resistance to emulsification and preservation stability, high hardness in the form of cure film of the composition, and excellent alkali developability, which is preferably an active energy beam-curable composition.

Means for Solving the Problems

In order to solve the above problems, the inventors found that a curable composition including a polyfunctional (meth) acrylate, which is obtained by conducting a transesterification reaction of a polyalcohol and a monofunctional (meth) acrylate with the combination use of a specific basic catalyst and a zinc-based catalyst, has a low level of viscosity, rapid curing ability in the form of thin film, and excellent hardness in the form of cured film. This has led to the completion of the invention.

The invention is explained in detail below.

The composition of the invention can be formed as having a low level of viscosity and rapid curing ability in the form of thin film, and further having excellent resistance to emulsification, preservation stability, high hardness in the form of cured film of the composition, and excellent alkali developability.

MODES FOR CARRYING OUT THE INVENTION

The invention relates to a curable composition including a mixture (A) of a polyfunctional (meth)acrylate obtained by conducting a transesterification reaction of a polyalcohol and a monofunctional (meth)acrylate under the presence of the following catalysts X and Y:

catalyst X: a compound that is at least one selected from the group consisting of cyclic tertiary amine having an azabicyclo structure or a salt or complex thereof, amidine or a salt or complex thereof, and a compound having a pyridine ring or a salt or complex thereof; and catalyst Y: a compound including zinc.

The component (A), the other components, and methods of using the same are explained below.

1. Component (A)

The component (A) is a mixture of a polyfunctional (meth)acrylate obtained by conducting a transesterification reaction of a polyalcohol and a monofunctional (meth) acrylate under the presence of the catalysts X and Y.

According to the transesterification reaction of a polyalcohol and a monofunctional (meth)acrylate conducted using the catalysts X and Y in combination, the component (A) contains a high-molecular-weight body in a fewer amount, compared with that in a dehydration esterification reaction of a polyalcohol and (meth)acrylic acid, and thus, the component (A) has a low level of viscosity and few impurities. Therefore, it becomes possible to produce the polyfunctional (meth)acrylate mixture having excellent physical properties described above.

Methods of producing a polyalcohol, a monofunctional (meth)acrylate, a catalyst X, a catalyst Y, and a component (A) are explained below.

1-1. Polyalcohol

A polyalcohol used as a starting material of the component (A) is a compound having at least two alcoholic hydroxyl groups in its molecule.

Specific examples of the component (A) include aliphatic alcohol, alicyclic alcohol, aromatic alcohol, and polyalcohol ether. The component (A) may have, in its molecule, different functional groups such as a phenolic hydroxyl group, a ketone group, an acyl group, an aldehyde group, a thiol group, an amino group, an imino group, a cyano group, a nitro group, a vinyl group and bonds such as an ether bond, an ester bond, a carbonate bond, an amide bond, an imide bond, a peptide bond, an urethane bond, an acetal bond, a hemiacetal bond, and a hemiketal bond.

Specific examples of divalent alcohol having two alcoholic hydroxyl groups include ethylene glycol, diethylene glycol, triethylene glycol, polyethylene glycol, propylene glycol, trimethylene glycol, dipropylene glycol, tripropylene glycol, polypropylene glycol, butanediol, pentanediol, hexanediol, heptanediol, nonanediol, neopentyl glycol, cyclohexanediol, cyclohexanedimethanol, dioxane glycol, N-methyldiethanolamine, N-ethyldiethanolamine, N-butyldiethanolamine, N-tert-butyldiethanolamine, N-lauryldiethanolamine, stearyldiethanolamine, N-phenyldiethanolamine, m-tolyldiethanolamine, p-tolyldiethanolamine, N,N'-bis(2-hydroxypropyl)aniline, N-nitrosodiethanolamine, N-(2-hydroxyethyl)lactamide, N,N'-bis(2-hydroxyethyl)oxamide, 3-morpholino-1,2-propanediol, 2,6-pyridinedimethanol, 3-(dimethyl amino)-1,2-propanediol, 3-(diethylamino)-1,2-propanediol, alloxane dihydrate, (+)-N,N,N',N'-tetramethyl-L-tartardiamide, (−)-N,N,N',N'-tetramethyl-D-tartardiamide, N-propyl-N-(2,3-dihydroxypropyl)perfluoro-n-octyl sulfonamide, thymidine, chloramphenicol, thiamphenicol, D-erythronolactone, methyl 4,6-O-benzylidene-α-D-glucopyranoside, phenyl 4,6-O-benzylidene-1-thio-β-D-glucopyranoside, 1,25,6-di-O-isopropylidene-D-mannitol, 1,2-O-isopropylidene-α-D-xylofuranose, 2,6-di-O-palmitoyl-L-ascorbic acid, isosorbide, and alkylene oxide adducts thereof, and further include alkylene oxide adducts of compounds having phenolic hydroxyl groups, such as hydroquinone, bisphenol A, bisphenol AP, bisphenol AF, bisphenol B, bisphenol BP, bisphenol C, bisphenol E, bisphenol F, bisphenol G, bisphenol M, bisphenol S, thiobisphenol, bisphenol P, bisphenol PH, bisphenol TMC, and bisphenol Z, and alcohol having a carbonate bond, such as polycarbonatediol.

Specific examples of trivalent alcohol having three alcoholic hydroxyl groups include trimethylolethane, trimethylolpropane, glycerin, tris(2-hydroxyethyl)isocyanurate, hexanetriol, octanetriol, decanetriol, triethanolamine, triisopropanol amine, 1-[bis2-(hydroxyethyl)amino]-2-propanol, D-panthenol, DL-panthenol, uridine, 5-methyluridine, cytidine, inosine, adenosine, leucomycin A3, leucomycin A4, leucomycin A6, leucomycin A8, clindamycin hydrochloride hydrate, prednisolone, methyl β-D-arabinopyranoside, methyl β-L-fucopyranoside, methyl α-L-fucopyranoside, D-galactal, 4-methoxyphenyl 3-O-allyl-β-D-galactopyranoside, 4-methoxyphenyl 3-O-benzyl-β-D-galactopyranoside, 1,6-anhydro-β-D-glucose, α-chloralose, β-chloralose, 4,6-O-ethylidene-α-D-glucopyranose, D-glucal, 1,2-O-isopropylidene-α-D-glucofuranose, D-glucurono-6,3-lactone, 2-deoxy-D-ribose, methyl β-D-ribofuranoside, D-(+)-ribono-1,4-lactone, methyl-β-D-xylopyranoside, 6-O-palmitoyl-L-ascorbic acid, 6-O-stearoyl-L-ascorbic acid, 3-O-ethyl-L-ascorbic acid, and alkylene oxide adducts thereof.

Specific examples of quadrivalent alcohol having four alcoholic hydroxyl groups include ditrimethylolethane, ditrimethylolpropane, diglycerin, pentaerythritol, N,N,N',N'-tetrakis(2-hydroxyethyl)butanediamide, N,N,N',N'-tetrakis(2-hydroxypropyl)butanediamide, N,N,N',N'-tetrakis(2-hydroxyethyl)hexanediamide, N,N,N',N'-tetrakis(2-hydroxypropyl)hexanediamide, N,N,N',N'-tetrakis(2-hydroxyethyl)ethylenediamine, N,N,N',N'-tetrakis(2-hydroxypropyl)ethylene diamine, N-hexanoyl-D-glucosamine, N-valeryl-D-glucosamine, N-trifluoroacetyl-D-glucosamine, N-benzoyl-D-glucosamine, 5-acetamide-N,N'-bis(2,3-dihydroxypropyl)-2,4,6-triiodoisophthalamide, spiramycin, clarithromycin, leucomycin A1, leucomycin A5, leucomycin A7, leucomycin A9, leucomycin A13, lincomycin hydrochloride monohydrate, diazolidinyl urea, D-(−)-arabinose, DL-arabinose, L-(+)-arabinose, meso-erythritol, D-(+)-fucose, L-(−)-fucose, allyl α-D-galactopyranoside, methyl β-D-galactopyranoside, methyl α-D-galactopyranoside monohydrate, 4-methoxyphenyl β-D-galactopyranoside, 2-nitrophenyl β-D-galactopyranoside, 4-nitrophenyl α-D-galactopyranoside, 4-nitrophenyl β-D-galactopyranoside, phenyl β-D-galactopyranoside, N-acetyl-D-galactosamine hydrate, D-(+)-galactosamine hydrochloride, arbutin, 2-deoxy-D-glucose, esculin 1.5-hydrate, D-(+)-glucono-1,5-lactone, D-glucuronamide, helicin, methyl α-D-glucopyranoside, methyl β-D-glucopyranoside 0.5-hydrate, 4-methoxyphenyl β-D-glucopyranoside, 4-nitrophenyl β-D-glucopyranoside monohydrate, 4-nitrophenyl α-D-glucopyranoside, nonyl β-D-glucopyranoside, n-octyl β-D-glucopyranoside, phenyl β-D-glucopyranoside hydrate, phlorhizin hydrate, piceid, puerarin, N-acetyl-D-glucosamine, N-benzoyl-D-glucosamine, D-(+)-glucosaminehydrochloride, N-hexanoyl-D-glucosamine, N-valeryl-D-glucosamine, L-(+)-gulonic acid γ-lactone, D-(−)-lyxose, L-(+)-lyxose, 3,4-O-isopropylidene-D-mannitol, methyl α-D-mannopyranoside, D-mannono-1,4-lactone, 4-methoxyphenyl α-D-mannopyranoside, N-acetyl-D-mannosamine monohydrate, D-(−)-ribose, L-ribose, D-(+)-xylose, DL-xylose, L-(−)-xylose, D-araboascorbic acid, L-ascorbic acid, L-threitol, and alkylene oxide adducts thereof.

Specific examples of pentavalent alcohol having five alcoholic hydroxyl groups include tritrimethylolethane, tritrimethylolpropane, triglycerin, bis(2-hydroxyethyl)amino-tris(hydroxymethyl)methane, bis(2-hydroxypropyl)amino-tris(hydroxymethyl)methane, N,N,N',N'',N''-pentakis(2-hydroxyethyl)diethylenetriamine, N,N,N',N'',N''-pentakis(2-hydroxypropyl)diethylenetriamine, miglitol, erythoromycin, azithromycin dihydrate, D-(+)-arabitol, DL-arabitol, L-(−)-arabitol, D-(−)-fructose, L-(+)-fructose, D-(+)-galactose, L-(−)-galactose, (3-D-glucose, D-(+)-glucose, L-(−)-glucose, D-glucosediethyl mercaptal, salicin, L-gulose, D-(+)-mannose, L-(−)-mannose, ribitol, L-(−)-sorbose, D-tagatose, xylitol, sucralose, glyceryl ascorbate, and alkylene oxide adducts thereof.

Specific examples of a polyalcohol having six or more alcoholic hydroxyl groups include polytrimethylolethane, polytrimethylolpropane, polyglycerin, dipentaerythritol, tripentaerythritol, polypentaerythritol, iohexol, galactitol, D-sorbitol, L-sorbitol, myo-inositol, scyllo-inositol, D-mannitol, L-mannitol, icariin, amygdalin, D-(+)-cellobiose, diosmin, 2-O-α-D-glucopyranosyl-L-ascorbic acid, hesperidin, D-(+)-lactose monohydrate, lactulose, D-(+)-maltose monohydrate, D-(+)-melibiose monohydrate, methylhesperidin, maltitol, naringin hydrate, neohesperidin dihydrochalcone hydrate, palatinose hydrate, rutin hydrate, D-(+)-sucrose, stevioside, D-(+)-turanose, D-(+)-trehalose (anhydrous), D-(+)-trehalose dihydrate, D-(+)-trehalose hydrate, D-(+)-raffinose pentahydrate, rebaudioside A, stachyose, α-cyclodextrin, β-cyclodextrin, γ-cyclodextrin, starch, polyvinyl alcohol, and alkylene oxide adducts thereof.

These polyalcohols may be used singly, or in any combination of two or more kinds thereof in the invention.

Of these polyalcohols, a polyalcohol having three or more alcoholic hydroxyl groups is preferable, and dipentaerythritol and pentaerythritol are particularly preferable in that hardness of a cured film of the obtained component (A) is high.

1-2. Monofunctional (Meth)Acrylate

A monofunctional (meth)acrylate used as a starting material for the component (A) is a compound having one (meth)acryloyl group in its molecule, for example, any compound represented by the following Formula (1).

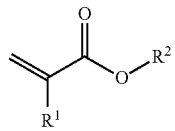

(1)

In Formula (1), $R^1$ represents a hydrogen atom or a methyl group. $R^2$ represents a $C_{1-50}$ organic group.

Specific examples of $R^2$ of the above-described Formula (1) include a methyl group, an ethyl group, an n- or i-propyl group, an n-, i- or t-butyl group, an n-, s- or t-amyl group, a neopentyl group, an n-, s-, or t-hexyl group, an n-, s-, or t-heptyl group, an n-, s-, or t-octyl group, a 2-ethylhexyl group, a capryl group, a nonyl group, a decyl group, an undecyl group, a lauryl group, a tridecyl group, a myristyl group, a pentadecyl group, a cetyl group, a heptadecyl group, a stearyl group, a nonadecyl group, an alkyl group, a seryl group, a myricyl group, a mericyl group, a vinyl group, an allyl group, a methallyl group, a crotyl group, a 1,1-dimethyl-2-propenyl group, a 2-methylbutenyl group, a 3-methyl-2-butenyl group, a 3-methyl-3-butenyl group, a 2-methyl-3-butenyl group, a butenyl group, a pentenyl group, a hexenyl group, a heptenyl group, an octenyl group, a nonenyl group, a decenyl group, an undecenyl group, a dodecenyl group, a tridecenyl group, a tetradecenyl group, a pentadecenyl group, a hexadecenyl group, a heptadecenyl group, an oleyl group, a linol group, a linolen group, a cyclopentyl group, a cyclopentylmethyl group, a cyclohexyl group, a cyclohexylmethyl group, a 4-methylcyclohexyl group, a 4-t-butylcyclohexyl group, a tricyclodecanyl group, an isobornyl group, an adamantyl group, a dicyclopentanyl group, a dicyclopentenyl group, a phenyl group, a methylphenyl group, a dimethylphenyl group, a trimethylphenyl group, a 4-t-butylphenyl group, a benzyl group, a diphenylmethyl group, a diphenylethyl group, a triphenylmethyl group, a cinnamyl group, a naphthyl group, an anthranil group, a methoxyethyl group, a methoxyethoxyethyl group, a methoxyethoxyethoxyethyl group, a 3-methoxybutyl group, an ethoxyethyl group, an ethoxyethoxyethyl group, a cyclopentoxyethyl group, a cyclohexyloxyethyl group, a cyclopentoxyethoxyethyl group, a cyclohexyloxyethoxyethyl group, a dicyclopentenyl oxyethyl group, a phenoxyethyl group, a phenoxyethoxyethyl group, a glycidyl group, a β-methylglycidyl group, a β-ethylglycidyl group, a 3,4- epoxy cyclohexylmethyl group, a 2-oxetanemethyl group, a 3-methyl-3-oxetanemethyl group, a 3-ethyl-3-oxetanemethyl group, a tetrahydrofuranyl group, a tetrahydrofurfuryl group, tetra hydropyranyl group, dioxazolinyl group, dioxanyl group, N,N-dimethylaminoethyl group, an N,N-diethyl-aminoethyl group, an N,N-dimethylaminopropyl group, an N,N-diethylaminopropyl group, an N-benzyl-N-methylaminoethyl group, and an N-benzyl-N-methylaminopropyl group.

Of these functional groups, $R^2$ is preferably a $C_{1-8}$ alkyl group such as a methyl group, an ethyl group, a propyl group, a pentyl group, a butyl group, a heptyl group, an octyl group, a heptyl group, or a 2-ethylhexyl group, an alkoxyalkyl group such as a methoxyethyl group, an ethoxyethyl group, or a methoxybutyl group, or a dialkyl amino group such as an N,N-dimethylaminoethyl group, an N,N-diethyl-aminoethyl group, an N,N-dimethylaminopropyl group, or N,N-diethylaminopropyl group.

These monofunctional (meth)acrylates may be used singly, or in any combination of two or more kinds thereof in the invention.

Of these monofunctional (meth)acrylates, alkyl(meth) acrylate having a $C_{1-8}$ alkyl group such as methyl(meth) acrylate, ethyl(meth)acrylate, n-butyl(meth)acrylate, i-butyl (meth)acrylate, or 2-ethylhexyl(meth)acrylate, alkoxyalkyl (meth)acrylate such as 2-methoxyethylacrylate, and N,N-dimethylaminoethyl(meth)acrylate are preferable, and (meth)acrylate having a $C_{1-4}$ alkyl group and alkoxyalkyl (meth)acrylate having a $C_{1-2}$ alkyl group, which show favorable reactivity to most of polyalcohols and readily available, are particularly preferable.

Further, alkoxyalkyl(meth)acrylate having a $C_{1-2}$ alkyl group, which promotes dissolution of polyalcohols and shows extremely favorable reactivity, is more preferable, and 2-methoxyethyl(meth)acrylate is particularly preferably.

Furthermore, acrylate is particularly preferable as a monofunctional (meth)acrylate because acrylate has excellent reactivity.

The proportions of a polyalcohol and a monofunctional (meth)acrylate used in a method of producing the component (A) are not particularly limited. However, the amount of a monofunctional (meth)acrylate is preferably from 0.4 to 10.0 mol and more preferably from 0.6 to 5.0 mol with respect to 1 mol in total of hydroxyl groups in a polyalcohol. It is possible to prevent a side reaction by setting the amount of monofunctional (meth)acrylate to 0.4 mol or more. It is also possible to increase the production of polyfunctional (meth)acrylate by setting the amount of monofunctional (meth)acrylate to 10.0 mol or less, thereby improving productivity.

1-3. Catalyst

As described above, the following catalysts X and Y are used in combination as transesterification reaction catalysts in the method of producing the component (A) because as the component (A) has low viscosity and few impurities as it contains a high-molecular-weight body in a small amount, which allows production of the above-described polyfunctional (meth)acrylate mixture having excellent physical properties.

Catalyst X: A compound that is at least one selected from the group consisting of cyclic tertiary amine having an azabicyclo structure or a salt or complex thereof (hereinafter referred to as "azabicyclo-based compound"), amidine or a salt or complex thereof (hereinafter referred to as "amidine-based compound"), and a compound having a pyridine ring or a salt or complex thereof (hereinafter referred to as "pyridine-based compound").

Catalyst Y: A compound including zinc.
Catalysts X and Y are explained below.
1-3-1. Catalyst X The catalyst X in the method of producing the component (A) is a catalyst that is at least one selected from the group consisting of an azabicyclo-based compound, an amidine-based compound, and a pyridine-based compound.

These compounds used as the catalyst X have excellent catalyst activity so that the component (A) can be preferably produced therefrom. In addition, the compounds each form a complex with a catalyst Y described below after the termination of reaction, and the complex can be readily removed from a reaction solution after the termination of reaction by a convenient method involving adsorption or the like. In particular, as a complex of an azacyclo-based compound with the catalyst Y is poorly soluble in the reaction solution, the complex can be removed more easily by, for example, filtration and adsorption.

Meanwhile, although a phosphine-based compound has excellent catalyst activity, the compound is unlikely to form a complex with the catalyst Y. Meanwhile, if a complex is formed, the complex is readily soluble in the reaction solution and the most part of the phosphine-based compound or complex remains dissolved in the reaction solution after the termination of reaction, which makes it difficult to remove the complex from the reaction solution by a convenient method involving, for example, filtration and adsorption. As a result, the phosphine-based catalyst remains in the final product. This results in problems of preservation stability such as turbidness or precipitation of a catalyst that appears during storage of a product or thickening or gelling that occurs over time. Also in a case in which the phosphine-based compound is used as a component of a composition, there are similar problems.

Specific examples of the azabicyclo-based compound include 1-azabicyclo[1,1,0]butane, 1,3-diazabicyclo[1,1,0] butane, 1-azabicyclo[2,1,0]heptane, 1,3-diazabicyclo[2,1,0] heptane, 1,4-diazabicyclo[2,1,0]heptane, 1-azabicyclo[2,2, 0]hexane, 1,3-diazabicyclo[2,2,0]hexane, 1-azabicyclo[2,1, 1]hexane, 1,3-diazabicyclo[2,1,1]hexane, 1-azabicyclo[2,2, 1]heptane, 1,3-diazabicyclo[2,2,1]heptane, 1,4-diazabicyclo [2,2,1]heptane, 1-azabicyclo[3,2,0]heptane, 1,3-diazabicyclo[3,2,0]heptane, 1,4-diazabicyclo[3,2,0]heptane, 1,6-diazabicyclo[3,2,0]heptane, 1,3-diazabicyclo[2,2,2]octane, 1-azabicyclo[3,2,1]octane, 1,3-diazabicyclo[3,2,1]octane, 1,4-diazabicyclo[3,2,1]octane, 1,5-diazabicyclo[3,2,1] octane, 1,6-diazabicyclo[3,2,1]octane, 1-azabicyclo[4,1,1] octane, 1,3-diazabicyclo[4,1,1]octane, 1,4-diazabicyclo[4,1, 1]octane, 1,5-diazabicyclo[4,1,1]octane, 1,6-diazabicyclo[4, 1,1]octane, 1,7-diazabicyclo[4,1,1]octane, 1-azabicyclo[4,2, 0]octane, 1,3-diazabicyclo[4,2,0]octane, 1,4-diazabicyclo[4, 2,0]octane, 1,5-diazabicyclo[4,2,0]octane, 1,7-diazabicyclo [4,2,0]octane, 1-azabicyclo[3,3,1]nonane, 1,3-diazabicyclo [3,3,1]nonane, 1,4-diazabicyclo[3,3,1]nonane, 1,5-diazabicyclo[3,3,1]nonane, 1-azabicyclo[3,2,2]nonane, 1,3-diazabicyclo[3,2,2]nonane, 1,4-diazabicyclo[3,2,2]nonane, 1,5-diazabicyclo[3,2,2]nonane, 1,6-diazabicyclo[3,2,2] nonane, 1,8-diazabicyclo[3,2,2]nonane, 1-azabicyclo[4,3,0] nonane, 1,3-diazabicyclo[4,3,0]nonane, 1,4-diazabicyclo[4, 3,0]nonane, 1,5-diazabicyclo[4,3,0]nonane, 1,6-diazabicyclo[4,3,0]nonane, 1,7-diazabicyclo[4,3,0]nonane, 1,8-diazabicyclo[4,3,0]nonane, 1-azabicyclo[4,2,1]nonane, 1,3-diazabicyclo[4,2,1]nonane, 1,4-diazabicyclo[4,2,1] nonane, 1,5-diazabicyclo[4,2,1]nonane, 1,6-diazabicyclo[4, 2,1]nonane, 1,7-diazabicyclo[4,2,1]nonane, 1-azabicyclo[5, 2,0]nonane, 1,3-diazabicyclo[5,2,0]nonane, 1,3-diazabicyclo[5,2,0]nonane, 1,4-diazabicyclo[5,2,0]nonane, 1,5-diazabicyclo[5,2,0]nonane, 1,6-diazabicyclo[5,2,0]nonane, 1,7-diazabicyclo[5,2,0]nonane, 1,8-diazabicyclo[5,2,0]nonane, 1-azabicyclo[5,1,1]nonane, 1,3-azabicyclo[5,1,1]nonane, 1,4-azabicyclo[5,1,1]nonane, 1,5-azabicyclo[5,1,1]nonane, 1,6-azabicyclo[5,1,1]nonane, 1,7-azabicyclo[5,1,1]nonane, 1-azabicyclo[6,1,0]nonane, 1,3-diazabicyclo[6,1,0]nonane, 1,4-diazabicyclo[6,1,0]nonane, 1,5-diazabicyclo[6,1,0]nonane, 1,6-diazabicyclo[6,1,0]nonane, 1,7-diazabicyclo[6,1,0]nonane, 1,8-diazabicyclo[6,1,0]nonane, 1-azabicyclo[7,1,0]decane, 1,9-diazabicyclo[7,1,0]decane, 1-azabicyclo[6,2,0]decane, 1,8-diazabicyclo[6,2,0]decane, 1-azabicyclo[6,1,1]decane, 1,8-diazabicyclo[6,1,1]decane, 1-azabicyclo[5,3,0]decane, 1,7-diazabicyclo[5,3,0]decane, 1-azabicyclo[5,2,1]decane, 1,7-diazabicyclo[5,2,1]decane, 1-azabicyclo[4,3,1]decane, 1,6-diazabicyclo[4,3,1]decane, 1-azabicyclo[4,2,2]decane, 1,6-diazabicyclo[4,2,2]decane, 1-azabicyclo[5,4,0]undecane, 1,7-diazabicyclo[5,4,0]undecane, 1-azabicyclo[5.3.1]undecane, 1,7-diazabicyclo[5,3,1]undecane, 1-azabicyclo[5,2,2]undecane, 1,7-diazabicyclo[5,2,2]undecane, 1-azabicyclo[4,4,1]undecane, 1,7-diazabicyclo[4,4,1]undecane, 1-azabicyclo[4,3,2]undecane, 1,7-diazabicyclo[4,3,2]undecane, 1-azabicyclo[3,3,0]octane, 1-azabicyclo[4,3,0]nonane, quinuclidine, lupinane, lupinine, quinolizidine, 3-hydroxyquinuclidine, 3-quinuclidinone, quincorine, quincoridine, cinchonidine, cinchonine, quinidine, kinin, cupreine, ibogaine, swainsonine, castanospermine, mianserin, mirtazapine, canadine, Troger's base, 1-azabicyclo[2,2,2]octane-3-carboxylic acid, triethylene diamine (also known as 1,4-diazabicyclo[2,2,2]octane, hereinafter referred to as "DABCO"), hexamethylenetetramine, 3-quinolidinone hydrochloride, 3-chloro-1-azabicyclo[2,2,2]octane hydrochloride, cinchonidine dihydrochloride, cinchonine hydrochloride hydrate, cinchonidine sulfate dihydrate, hydroquinidine hydrochloride, cinchonine sulfate dihydrate, quinine hydrochloride dihydrate, quinine sulfate dihydrate, quinine phosphate, quinidine sulfate dihydrate, mianserin hydrochloride, 1,1'-(butane-1,4-diyl)bis[4-aza-1-azoniabicyclo[2,2,2]octane]dibromide, 1,1'-(decane-1,10-diyl)bis[4-aza-1-azoniabicyclo[2,2,2]octane]dibromide, bis(trimethyl aluminum)-1,4-diazabicyclo[2,2,2]octane adduct, bismuthine, quinuclidine hydrochloride, 3-quinuclidinone hydrochloride, 3-hydroxyquinuclidine hydrochloride, DABCO hydrochloride, quinuclidine acetate, 3-quinuclidinone acetate, 3-hydroxyquinuclidine acetate, DABCO acetate, quinuclidine acrylic acid salt, 3-quinuclidinone acrylic acid salt, 3-hydroxyquinuclidine acrylic acid salt, and DABCO acrylic acid salt.

Specific examples of the amidine-based compound include imidazole, N-methylimidazole, N-ethylimidazole, 1-benzyl-2-methylimidazole, 1-benzyl-2-phenylimidazole, 1-vinyl imidazole, 1-allylimidazole, 1,8-diazabicyclo[5,4,0]undeca-7-ene (hereinafter referred to as "DBU"), 1,5-diazabicyclo[4,3,0]nona-5-ene (hereinafter referred to as "DBN"), N-methylimidazole hydrochloride, DBU hydrochloride, DBN hydrochloride, N-methylimidazole acetate, DBU acetate, DBN acetate, N-methylimidazole acrylic acid salt, DBU acrylic acid salt, DBN acrylic acid salt, and phthalimide DBU.

Specific examples of the pyridine-based compound include pyridine, 2-methylpyridine, 3-methylpyridine, 4-methylpyridine, 2-ethylpyridine, 3-ethylpyridine, 4-ethylpyridine, 2-propylpyridine, 4-propylpyridine, 4-isopropylpyridine, 4-tert-butylpyridine, 4-amyl pyridine, 4-(1-ethylpropyl)pyridine, 4-(5-nonyl)pyridine, 2-vinyl pyridine, 2,3-dimethylpyridine, 2,4-dimethylpyridine, 2,5-dimethylpyridine, 2,6-dimethylpyridine, 3,4-dimethylpyridine, 3,5-dimethylpyridine, 3,5-diethylpyridine, N,N-dimethyl-4-aminopyridine (hereinafter referred to as "DMAP"), 2,4,6-trimethylpyridine, 2,6-di-tert-butylpyridine, N,N-dimethyl-2-aminopyridine, 4-piperidinopyridine, 4-pyrrolidinopyridine, 4-phenylpyridine, quinoline, 2-methylquinoline, 3-methylquinoline, 4-methylquinoline, 6-methylquinoline, 7-methylquinoline, 8-methylquinoline, isoquinoline, 1-methylisoquinoline, acridine, 3,4-benzoquinoline, 5,6-benzoquinoline, 7,8-benzoquinoline, 2-hydroxypyridine, 3-hydroxypyridine, 4-hydroxypyridine, 2,6-dihydroxypyridine, 2-(hydroxymethyl)pyridine, 3-(hydroxymethyl)pyridine, 4-(hydroxymethyl)pyridine, 5-hydroxyisoquinoline, 2-methoxypyridine, 3-methoxypyridine, 4-methoxypyridine, 2,6-dimethoxypyridine, 1,5-naphthyridine, 1,6-naphthyridine, 1,7-naphthyridine, 1,8-naphthyridine, 2,6-naphthyridine, 2,7-naphthyridine, 2,2'-bipyridyl, 3,3'-bipyridyl, 4,4'-bipyridyl, 2,3'-bipyridyl, 2,4'-bipyridyl, 3,4'-bipyridyl, 4,4'-ethylenedipyridine, 1,3-di(4-pyridyl)propane, 1,10-phenanthroline monohydrate, 2-(trimethylsilyl)pyridine, DMAP hydrochloride, DMAP acetate, DMAP acrylic acid salt, 1-methylpyridinium chloride, 1-propylpyridinium chloride, a borane-pyridine complex, a borane-2-picoline complex, and p-toluenesulfonic acid pyridinium.

These catalysts X may be used singly, or in any combination of two or more kinds thereof in the invention. Of these catalysts X, quinuclidine, 3-quinuclidinone, 3-hydroxyquinuclidine, DABCO, N-methylimidazole, DBU, DBN, and DMAP are preferable, and 3-hydroxyquinuclidine, DABCO, N-methylimidazole, DBU, and DMAP, which show favorable reactivity to most of polyalcohols and readily available, are particularly preferable.

The amount of the catalyst X used in the method of producing the component (A) is not particularly limited. However, the amount of the catalyst X used is preferably from 0.0001 to 0.5 mol and more preferably from 0.0005 to 0.2 mol with respect to 1 mol in total of hydroxyl groups in a polyalcohol. It is possible to increase the production of polyfunctional (meth)acrylate of interest by using the catalyst X in an amount of 0.0001 mol or more. It is also possible to prevent generation of by-products or coloring of the reaction solution by setting the amount to 0.5 mol or less, thereby simplifying the purification step after the termination of reaction.

1-3-2. Catalyst Y

The catalyst Y is a compound including zinc.

As the catalyst Y, various compounds can be used as long as they include zinc. However, organic acid zinc and zinc diketone enolate are preferable as they have excellent reactivity. Examples of organic acid zinc include dibasic acid zinc such as zinc oxalate and any compound represented by the following Formula (3).

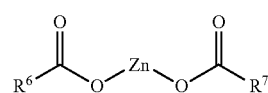

(3)

In Formula (3), $R^6$ and $R^7$ each represent a $C_{1-20}$ linear or branched alkyl group, a $C_{1-20}$ linear or branched alkenyl group, a $C_{6-24}$ aryl group, or a $C_{5-20}$ cycloalkyl group. $R^6$ and $R^7$ may be the same or different.

As the compound represented by Formula (3), a compound in which $R^6$ and $R^7$ each represent a $C_{1-20}$ linear or branched alkyl group is preferable. Regarding $R^6$ and $R^7$, a $C_{1-20}$ linear or branched alkyl group is a functional group having no halogen atom such as fluorine or chlorine and the catalyst Y having such functional group is preferable because a polyfunctional (meth)acrylate can be produced at a high yield.

Examples of zinc diketone enolate include a compound represented by the following Formula (4).

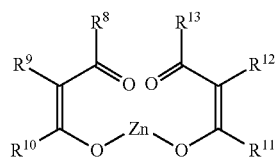

In Formula (4), $R^8$, $R^9$, $R^{10}$, $R^{11}$, $R^{12}$, and $R^{13}$ each represent a hydrogen atom, a $C_{1-20}$ linear or branched alkyl group, a $C_{1-20}$ linear or branched alkenyl group, a $C_{6-24}$ aryl group, or a $C_{5-20}$ cycloalkyl group. $R^8$, $R^9$, $R^{10}$, $R^{12}$ and $R^{13}$ may be the same or different.

Specific examples of the compound including zinc represented by Formula (3) described above include zinc acetate, zinc acetate dihydrate, zinc propionate, zinc octylate, zinc neodecanoate, zinc laurate, zinc myristate, zinc stearate, zinc cyclohexane butyrate, 2-ethylhexanoic acid zinc, zinc benzoate, t-butyl zinc benzoate, zinc salicylate, zinc naphthenate, zinc acrylate, and zinc methacrylate.

In a case in which any of these compounds including zinc forms a complex with a hydrate or solvate thereof or the catalyst X, the complex with the hydrate or solvate thereof or the catalyst X may be used as the catalyst Y in the method of producing the component (A).

Specific examples of the compound including zinc represented by Formula (4) described above include zinc acetylacetonate, zinc acetylacetonate hydrate, bis(2,6-dimethyl-3,5-heptanedionate)zinc, bis(2,2,6,6-tetramethyl-3,5-heptanedionate)zinc, and bis(5,5-dimethyl-2,4-hexanedionate)zinc. In a case in which any of these compounds including zinc forms a complex with a hydrate or solvate thereof or the catalyst X, the complex with the hydrate or solvate thereof or the catalyst X may be used as the catalyst Y in the method of producing the component (A).

As organic acid zinc and zinc diketone enolate in the catalyst Y, the compounds described above can be directly used or these compounds may be generated in a reaction system so as to be used.

For example, a zinc compound (hereinafter referred to as "material zinc compound") such as metal zinc, oxidized zinc, zinc hydroxide, zinc chloride, or zinc nitrate is used as a starting material. In the case of organic acid zinc, a method of reacting a material zinc compound and organic acid is employed. In the case of zinc diketone enolate, a method of reacting a material zinc compound and 1,3-diketone is employed.

These catalysts Y may be used singly, or in any combination of two or more kinds thereof in the invention. Of these catalysts Y, zinc acetate, zinc propionate, zinc acrylate, zinc methacrylate, and zinc acetylacetonate are preferable. Zinc acetate, zinc acrylate, and zinc acetylacetonate, which show favorable reactivity to most of polyalcohols and readily available, are particularly preferable.

The amount of the catalyst Y used in the method of producing the component (A) is not particularly limited. However, the amount of the catalyst Y is preferably from 0.0001 to 0.5 mol and more preferably from 0.0005 to 0.2 mol with respect to 1 mol in total of hydroxyl groups in a polyalcohol. It is possible to increase the production of polyfunctional (meth)acrylate of interest by using the catalyst Y in an amount of 0.0001 mol or more. It is also possible to prevent generation of by-products or coloring of the reaction solution by setting the amount to 0.5 mol or less, thereby simplifying the purification step after the termination of reaction.

1-4. Method of Producing Component (A)

The component (A) is produced by conducting a transesterification reaction of a polyalcohol and a monofunctional (meth)acrylate under the presence of the catalysts X and Y.

The amounts of the catalysts X and Y used in the method of producing the component (A) are not particularly limited. However, the amount of the catalyst X used is preferably from 0.005 to 10.0 mol and more preferably from 0.05 to 5.0 mol with respect to 1 mol of the catalyst Y. It is possible to increase the production of polyfunctional (meth)acrylate of interest by using the catalyst X in an amount of 0.005 mol or more. It is also possible to prevent generation of by-products or coloring of the reaction solution by setting the amount to 10.0 mol or less, thereby simplifying the purification step after the termination of reaction.

A preferable combination of catalysts X and Y used in the invention is a combination of an azabicyclo-based compound as the catalyst X and a compound represented by Formula (3) described above as the catalyst Y. Further, a combination of DABCO as an azabicyclo-based compound and zinc acetate and/or zinc acrylate as a compound represented by Formula (3) described above is most preferable.

This combination is favorably employed for various industrial purposes with priority on color tone because a polyfunctional (meth)acrylate can be obtained at a high yield, and the excellent color tone can be achieved after the termination of reaction. Further, as the catalysts are available at relatively inexpensive prices, the production method is economically advantageous.

The catalysts X and Y used in the invention may be added at the beginning of or in the middle of the reaction described above. Alternatively, the desired amounts of the catalysts used may be added at once or in divided portions.

The reaction temperature in the method of producing the component (A) is preferably from 40° C. to 180° C. and more preferably from 60° C. to 160° C. It is possible to increase the reaction rate by setting the reaction temperature to not less than 40° C. It is also possible to prevent thermal polymerization of (meth)acryloyl groups in the starting material or product or coloring of the reaction solution by setting the reaction temperature to not more than 180° C., thereby simplifying the purification step after the termination of reaction.

The reaction pressure in the method of producing the component (A) is not particularly limited as long as a certain reaction temperature can be maintained. The reaction may be conducted under reduced pressure or pressurized conditions. The reaction pressure is usually from 0.000001 to 10 MPa (absolute pressure).

In the method of producing the component (A), as the transesterification reaction proceeds, a monovalent alcohol derived from a monofunctional (meth)acrylate is generated as a by-product. The monovalent alcohol may coexist in the reaction system. However, progress in the transesterification reaction can be further promoted by discharging the monovalent alcohol outside of the reaction system.

It is also possible to conduct the reaction without using solvents in the method of producing the component (A). Solvents may be used, if necessary.

Specific examples of solvents include: hydrocarbons such as n-hexane, cyclohexane, methylcyclohexane, n-heptane, n-octane, n-nonane, n-decane, benzene, toluene, xylene, ethylbenzene, diethylbenzene, isopropylbenzene, amylbenzene, diamylbenzene, triamylbenzene, dodecylbenzene, didodecylbenzene, amyltoluene, isopropyltoluene, decalin, and tetralin; ethers such as diethylether, dipropylether, diisopropylether, dibutylether, diamylether, diethylacetal, dihexylacetal, t-butylmethylether, cyclopentylmethylether, tetrahydrofuran, tetrahydropyran, trioxane, dioxane, anisole, diphenylether, dimethylcellosolve, diglyme, triglyme, and tetraglyme; crown ethers such as 18-crown-6; esters such as methyl benzoate and γ-butyrolactone; ketones such as acetone, methylethylketone, methylisobutylketone, cyclohexanone, acetophenone, and benzophenone; carbonate compounds such as dimethyl carbonate, diethyl carbonate, ethylene carbonate, propylene carbonate, and 1,2-butylene carbonate; sulfones such as sulfolane; sulfoxides such as dimethyl sulfoxide; ureas or derivatives thereof; ionic liquids of phosphine oxides such as tributylphosphine oxide, imidazolium salts, piperidinium salts, and pyridinium salts; silicon oil; and water.

Of these solvents, hydrocarbons, ethers, carbonate compounds, and ionic liquids are preferable. These solvents may be used singly, or in any combination of two or more kinds thereof as a mix solvent.

In the method of producing the component (A), an inert gas such as argon, helium, nitrogen, or carbon dioxide may be introduced into the system in order to favorably maintain the color tone of the reaction solution. Alternatively, an oxygen-containing gas may be introduced in to the system in order to prevent polymerization of (meth)acryloyl groups. Specific examples of an oxygen-containing gas include air, a mix gas of oxygen and nitrogen, and a mix gas of oxygen and helium. As a method of introducing an oxygen-containing gas, a method of dissolving a gas in a reaction solution or infusing (i.e., bubbling) a gas into a reaction solution is employed.

In the method of producing the component (A), it is preferable to add a polymerization inhibitor in order to prevent polymerization of (meth)acryloyl groups.

Specific examples of a polymerization inhibitor include: organic polymerization inhibitors such as hydroquinone, tert-butyl hydroquinone, hydroquinone monomethylether, 2,6-di-tert-butyl-4-methylphenol, 2,4,6-tri-tert-butylphenol, 4-tert-butylcatechol, benzoquinone, phenothiazine, N-nitroso-N-phenyl hydroxylamine ammonium, 2,2,6,6-tetramethylpiperidine-1-oxyl, and 4-hydroxy-2,2,6,6-tetramethylpiperidine-1-oxyl; inorganic polymerization inhibitors such as copper chloride, copper sulfate, and iron sulfate; and organic salt-based polymerization inhibitors such as copper dibutyldithiocarbamate and N-nitroso-N-phenylhydroxylamine aluminum salt.

Polymerization inhibitors may be added singly, or in any combination of two or more kinds thereof. They may be added at the beginning of or in the middle of the invention. In addition, the desired amount of polymerization inhibitors used may be added at once or in divided portions or may be added continuously via a rectifier.

The proportion of a polymerization inhibitor to be added is preferably from 5 to 30,000 wt ppm and more preferably from 25 to 10,000 wt ppm in a reaction solution. When the proportion is set to 5 wt ppm or more, polymerization inhibition effects can be obtained. When the proportion is set to 30,000 wt ppm or less, coloring of a reaction solution can be prevented, and the purification step after the termination of reaction can be simplified. In addition, reduction of the curing rate of the obtained component (A) can be prevented.

The reaction time in the method of producing the component (A) varies depending on types of catalysts, the amounts of catalysts used, reaction temperature, reaction pressure, and so on. It is usually from 0.1 to 150 hours and preferably from 0.5 to 80 hours.

The method of producing the component (A) can be carried out by any of batch-type, semi-batch-type, and continuous-type methods. One example of the batch-type method can be carried out by introducing a polyalcohol, a monofunctional (meth)acrylate, catalysts, and polymerization inhibitors into a reactor, stirring a reaction solution while bubbling with an oxygen-containing gas at a certain temperature, and then discharging monovalent alcohol obtained as a by-product with progress in the transesterification reaction under a certain pressure from the reactor, thereby generating the component (A) of interest.

It is preferable to perform a separation/purification operation on a reaction product obtained in the method of producing the component (A) so that a polyfunctional (meth)acrylate of interest can be obtained with sufficient purity.

Examples of the separation/purification operation include a crystallization operation, a filtration operation, a distillation operation, and an extraction operation. It is preferable to combine these operations. Examples of a crystallization operation include cool crystallization and condensation crystallization. Examples of a filtration operation include pressurized filtration, suction filtration, and centrifugal filtration. Examples of a distillation operation include single distillation, fractional distillation, molecular distillation, and steam distillation. Examples of an extraction operation include solid-liquid extraction and liquid-liquid extraction.

Solvents may be used in the separation/purification operation. It is also possible to use a neutralizer for neutralizing catalysts and/or polymerization inhibitors used in the invention, adsorbents for removing the same by adsorption, acid and/or alkali for decomposing or removing by-products, activated carbon for improving the color tone, diatomaceous earth for improving filtration efficiency and the filtration rate, and the like.

1-5. Preferable Component (A)

The component (A) is a mixture of a polyfunctional (meth)acrylate obtained via transesterification reaction of a polyalcohol and a monofunctional (meth)acrylate, which is a mixture of a polyfunctional (meth)acrylate having no hydroxyl groups and a polyfunctional (meth)acrylate having hydroxyl groups.

For example, in the case of dipentaerythritol which is a preferable polyalcohol, the component (A) is a mixture of dipentaerythritol di(meth)acrylate, dipentaerythritol tri(meth)acrylate, dipentaerythritol tetra(meth)acrylate, dipentaerythritol penta(meth)acrylate, and dipentaerythritol hexa (meth)acrylate. In this case, a (meth)acrylate mixture of dipentaerythritol penta(meth)acrylate and dipentaerythritol hexa(meth)acrylate as main components is preferable. In addition, in the case of pentaerythritol which is another preferable polyalcohol, the component (A) is a mixture of pentaerythritol di(meth)acrylate, pentaerythritol tri(meth) acrylate, and pentaerythritol tetra(meth)acrylate. In this case, a mixture of pentaerythritol tetra(meth)acrylate as a main component is preferable.

A mixture of a polyfunctional (meth)acrylate may contain a small amount of mono(meth)acrylate.

The hydroxyl valence of the component (A) can be set depending on purposes, if appropriate.

In a case in which the component (A) is used for preferred purposes such as the use in a coating agent, ink, pattern formation, etc., the hydroxyl valence is preferably low. Specifically, the hydroxyl valence is preferably not more than 60 mg KOH/g and more preferably not more than 45 mg KOH/g.

It is possible to obtain a low-viscosity composition by setting the hydroxyl valence of the component (A) within the above range, thereby obtaining a composition with excellent cured product hardness.

The term "valence of hydroxyl group" used in the invention refers to the value of milligram (mg) of potassium hydroxide in an amount equivalent to the amount of hydroxyl groups in 1 g of a sample.

As described above, the component (A) is a mixture of different polyfunctional (meth)acrylates. It is preferable to use one with a low proportion of a high-molecular-weight body as a side reaction product.

For a high-molecular-weight body in the component (A), the area percent (%) of the high-molecular-weight body defined by the following Formula (1), which is a value obtained by gel permeation chromatography (hereinafter referred to as "GPC") measurement, is preferably less than 30%.

$$\text{Area percent of high-molecular-weight body}(\%) = [(R-I-L)/R] \times 100 \quad (1)$$

Symbols and terms used in Formula (1) have the following meanings.

R: Total area of detection peaks in the component (A)
I: Area of detection peaks including ideal-structure (meth)acrylate
L: Total area of detection peaks with a weight-average molecular weight (hereinafter referred to as "Mw") smaller than that for detection peaks including ideal-structure (meth)acrylate
Ideal structure (meth)acrylate: Polyfunctional (meth)acrylate that includes, in its molecule, (meth)acryloyl groups as many as hydroxyl groups included in one molecule of material alcohol and does not have a Michael addition-type structure Specific examples of ideal-structure (meth)acrylate include, as preferable polyalcohols, dipentaerythritol hexa(meth)acrylate in the case of dipentaerythritol, and pentaerythritol tetra(meth)acrylate in the case of pentaerythritol.

Note that, Mw in the invention refers to a value obtained by converting a molecular weight measured by GPC using tetrahydrofuran (hereinafter referred to as "THF") as a solvent with reference to the molecular weight of polystyrene.

By setting the area percent (%) of a high-molecular-weight body within the above range, it is possible to achieve low viscosity, thereby obtaining a composition having excellent cured film hardness.

The molecular weight measured by GPC in the invention means a value measured under the following conditions.

Detector: Differential refractometer (RI detector)
Column type: Crosslinked polystyrene column
Column temperature: From 25° C. to 50° C.
Eluent: THF 2. Curable Composition The invention relates to a curable composition including the component (A).

As the method of producing the composition, a production method including a step of producing a mixture of a polyfunctional (meth)acrylate by conducting a transesterification reaction of a polyalcohol and a monofunctional (meth)acrylate under the presence of the catalysts X and Y is preferable.

According to the production method, the component (A) can be produced at a high yield. In addition, as the obtained component (A) contains a small amount of a high-molecular-weight body, the component has low viscosity and contains few impurities. Therefore, the obtained composition has various excellent physical properties, which is preferable.

The step may be carried out in accordance with the method of producing the component (A). Viscosity of the composition can be set depending on purposes, if appropriate.

In a case in which the component (A) is used for preferred purposes such as the use in a coating agent, ink, and pattern formation, etc., viscosity of the composition can be set depending on purposes, if appropriate, which is preferably from 1 to 100,000 mPa·s and more preferably from 5 to 50,000 mPa·s. By setting the viscosity within such range, the composition is allowed to have an excellent leveling property of upon coating and a cured product thereof is allowed to have excellent appearance.

The term "viscosity" in the invention means a value measured using a type E viscometer at 25° C.

The composition of the invention can be used for both of an active energy beam-curable composition and a thermosetting composition. However, an active energy beam-curable composition is preferable.

The composition of the invention includes the above-described (A) as an essential component. However, various components can be mixed therewith depending on purposes.

Specifically, examples of other components include a photopolymerization initiator (hereinafter referred to as "component (B)"), a thermal polymerization initiator (hereinafter referred to as "component (C)"), a compound having unsaturated ethylene groups other than the component (A) (hereinafter referred to as "component (D)"), and an organic solvent (hereinafter referred to as "component (E)").

These components are explained below.

As the other components described below, the exemplified compounds may be used singly, or in combination of two or more kinds thereof.

2-1. Component (B)

In a case in which the composition of the invention is used as an active energy beam-curable composition and is further used as an electron beam-curable composition, it is also possible to allow the composition not to include the component (B) (photopolymerization initiator) so as to be cured by an electron beam.

In a case in which the composition of the invention is used as an active energy beam-curable composition especially using ultraviolet ray and visible ray as an active energy beam, it is preferable for the composition to further contain the component (B) in view of the ease of curing and cost.

In a case in which an electron beam is used as an active energy beam, it is not always necessary to blend the component (B). However, it is possible to blend a small amount of the component (B) in order to improve cuing, if necessary.

Specific examples of the component (B) include: aromatic ketone compounds such as benzyldimethylketal, benzyl, benzoin, benzoinethyl ether, benzoinisopropylether, benzoinisobutylether, 1-hydroxycyclohexylphenylketone, 2-hydroxy-2-methyl-1-phenylpropane-1-one, 1-[4-(2-hydroxyethoxy)phenyl]-2-hydroxy-2-methyl-1-propane-1-one, oligo[2-hydroxy-2-methyl-1-[4-1-(methylvinyl)phenyl]propanone, 2-hydroxy-1-[4-[4-(2-hydroxy-2-methyl-propionyl)

benzyl]phenyl]-2-methylpropane-1-one, 2-methyl-1-[4-(methylthio)]phenyl]-2-morpholinopropane-1-one, 2-benzyl-2-dimethylamino-1-(4-morpholinophenyl)butane-1-one, 2-dimethylamino-2-(4-methylbenzyl)-1-(4-morpholine-4-yl-phenyl)butane-1-one, 3,6-bis(2-methyl-2-morpholinopropionyl)-9-n-octyl carbazole, phenylglyoxylic acid methyl, ethylanthraquinone, and phenanthrenequinone; benzophenone-based compounds such as benzophenone, 2-methylbenzophenone, 3-methylbenzophenone, 4-methylbenzophenone, 2,4,6-trimethylbenzophenone, 4-phenylbenzophenone, 4-(methylphenylthio)phenylphenylmethane, methyl-2-benzophenone, 1-[4-(4-benzoylphenylsulfanyl) phenyl]-2-methyl-2-(4-methylphenylsulfonyl)propane-1-one, 4,4'-bis(dimethylamino)benzophenone, 4,4'-bis(diethylamino)benzophenone, and 4-methoxy-4'-dimethylaminobenzophenone; acyl phosphine oxide compounds such as bis(2,4,6-trimethylbenzoyl)phenylphosphine oxide, 2,4,6-trimethylbenzoyldiphenylphosphine oxide, ethyl (2,4,6-trimethylbenzoyl)phenylphosphinate, and bis(2,6-dimethoxybenzoyl)-2,4,4-trimethylpentylphosphine oxide; and thioxanthone-based compounds such as thioxanthone, 2-chlorothioxanthone, 2,4-diethylthioxanthone, isopropylthioxanthone, 1-chloro4-propylthioxanthone, 3-[3,4-dimethyl-9-oxo-9H-thioxanthone-2-yl-oxy]-2-hydroxypropyl-N,N,N-trimethylammonium chloride, and fluorothioxanthone.

Among these compounds, α-hydroxyphenylketones are preferable because surface curing ability is excellent in the atmosphere even for thin film coating. Specifically, 1-hydroxycyclohexylphenylketone and 2-hydroxy-2-methyl-1-phenyl-propane-1-one are more preferable.

In addition, in a case in which it is necessary to increase the film thickness of a cured film to, for example, not less than 50 μm, or in a case in which ultraviolet absorbers and colorants are used in combination in order to improve curing inside of a cured film, acyl phosphine oxide compounds such as bis(2,4,6-trimethylbenzoyl)-phenylphosphine oxide, 2,4,6-trimethylbenzoyldiphenylphosphine oxide, ethyl-(2,4,6-trimethylbenzoyl)phenylphosphinate, and bis(2,6-dimethoxybenzoyl)-2,4,4-trimethylpentylphosphine oxide, and also 2-methyl-1-[4-(methylthio)]phenyl]-2-morpholinopropane-1-one, 2-benzyl-2-dimethylamino-1-(4-morpholinophenyl)butane-1-one, 2-dimethylamino-2-(4-methylbenzyl)-1-(4-morpholine-4-yl-phenyl)-butane-1-one, and the like are preferably used in combination.

The content rate of the component (B) with respect to 100 parts by weight in total of a curable component is preferably from 0.1 to 10 parts by weight and more preferably from 0.5 to 8 parts by weight. By setting the content rate of the component (B) to not less than 0.1 parts by weight, the composition is allowed to have favorable photocurability and excellent adhesiveness. By setting the content rate of the component (B) to not more than 10 parts by weight, favorable internal curing inside of a cured film is achieved, thereby improving adhesion to a base material. The term "curable component" in the invention means a component that is cured with heat or active energy beam, which is a component (A), and it means components (A) and (D) in a case in which the component (D) described below is blended.

2-2. Component (C)

In a case in which the composition of the invention is used as a thermosetting composition, a thermal polymerization initiator can be blended therewith.

A variety of compounds can be used as thermal polymerization initiators. Organic peroxide and an azo-based initiator are preferable.

Specific examples of organic peroxide include 1,1-bis(t-butylperoxy)2-methylcyclohexane, 1,1-bis(t-hexylperoxy)-3,3,5-trimethylcyclohexane, 1,1-bis(t-hexylperoxy)cyclohexane, 1,1-bis(t-butylperoxy)-3,3,5-trimethylcyclohexane, 1,1-bis(t-butylperoxy)cyclohexane, 2,2-bis(4,4-di-butylperoxycyclohexyl)propane, 1,1-bis(t-butylperoxy)cyclododecane, t-hexylperoxyisopropyl monocarbonate, t-butylperoxymaleic acid, t-butylperoxy-3,5,5-trimethylhexanoate, t-butylperoxylaurate, 2,5-dimethyl-2,5-di(m-toluoylperoxy) hexane, t-butylperoxyisopropyl monocarbonate, t-butylperoxy2-ethylhexylmonocarbonate, t-hexylperoxybenzoate, 2,5-di-methyl-2,5-di(benzoylperoxy)hexane, t-butylperoxyacetate, 2,2-bis(t-butylperoxy)butane, t-butylperoxybenzoate, n-butyl-4,4-bis(t-butylperoxy)valerate, di-t-butylperoxyisophthalate, α,α'-bis(t-butylperoxy) diisopropylbenzene, dicumylperoxide, 2,5-dimethyl-2,5-di(t-butylperoxy)hexane, t-butylcumyl peroxide, di-t-butyl peroxide, p-menthane hydroperoxide, 2,5-dimethyl-2,5-di(t-butylperoxy)hexine-3, diisopropylbenzene hydroperoxide, t-butyltrimethylsilyl peroxide, 1,1,3,3-tetra methylbutyl hydroperoxide, cumene hydroperoxide, t-hexyl hydroperoxide, and t-butyl hydroperoxide.

Specific examples of an azo-based compound include 1,1'-azobis(cyclohexane-1-carbonitrile), 2-(carbamoylazo) isobutyronitrile, 2-phenylazo-4-methoxy-2,4-dimethylvaleronitrile, azo-di-t-octane, and azo-di-t-butane.

They may be used singly, or in combination of two or more kinds thereof. Alternatively, organic peroxide may be used in combination with a reductant in redox reaction.

The amounts of these thermal polymerization initiators used are preferably not more than 10 parts by weight with respect to 100 parts by weight in total of the curable component. In a case in which a thermal polymerization initiator is used singly, it can be used in accordance with ordinary means of usual radical thermal polymerization. In some cases, it is also possible to use a thermal polymerization initiator in combination with a component (B) (photopolymerization initiator) and conduct photo-curing and then further conduct thermal curing in order to improve the reaction rate.

2-3. Component (D)

The component (D) is an unsaturated ethylene compound other than the component (A) and it is blended in order to impart various physical properties to a cured product of the composition. Examples of unsaturated ethylene groups in the component (D) include a (meth)acryloyl group, a (meth) acrylamide group, a vinyl group, and a (meth)allyl group, and a (meth)acryloyl group is preferable.

The term "monofunctional" used hereinafter refers to a compound having one unsaturated ethylene group, the term "n-functional" refers to a compound having n number of unsaturated ethylene groups, and the term "polyfunctional" refers to a compound having two or more unsaturated ethylene groups.

Regarding the component (D), specific examples of a monofunctional unsaturated ethylene compound include compounds similar to monofunctional (meth)acrylates. Methyl(meth)acrylate, ethyl(meth)acrylate, butyl(meth) acrylate, 2-ethylhexyl(meth)acrylate, cyclohexyl(meth) acrylate, tert-butylcyclohexyl(meth)acrylate, and 2-methoxyethylacrylate are preferable.

Examples of compounds other than monofunctional (meth)acrylates described above include Michael addition-type dimers of (meth)acrylic acid and acrylic acid, ω-carboxy-polycaprolactone mono(meth)acrylate, phthalic acid monohydroxyethyl(meth)acrylate, ethylcarbitol(meth)acrylate, butylcarbitol(meth)acrylate, 2-ethylhexylcarbitol (meth)acrylate, benzyl(meth)acrylate, phenyl(meth)acrylate, (meth)acrylate of a phenol alkylene oxide adduct, (meth)acrylate of an alkylphenol alkylene oxide adduct, 2-hydroxyethyl(meth)acrylate, 2-hydroxypropyl(meth)acrylate, 4-hydroxybutylacrylate, (meth)acrylate of a paracumylphenol alkylene oxide adduct, orthophenylphenol(meth)acrylate, (meth)acrylate of an orthophenylphenol alkylene oxide adduct, tetrahydrofurfuryl(meth)acrylate, isobornyl (meth)acrylate, tricyclodecanemethylol(meth)acrylate, 2-hydroxy-3-phenoxypropyl(meth)acrylate, N-(2-(meth) acryloyloxyethyl)hexahydrophthalimide, N-(2-(meth)acryloyloxyethyl)tetrahydrophthalimide, N,N-dimethylacrylamide, acryloyl morpholine, N-vinyl pyrrolidone, and N-vinyl caprolactam.

As a bifunctional (meth)acrylate compound, epoxy(meth) acrylate having a bisphenol skeleton, polyether skeleton, or polyalkylene skeleton, urethane(meth)acrylate having a polyester skeleton, polyether skeleton or polycarbonate skeleton, polyester(meth)acrylate, and the like can be used.

In addition, a bifunctional (meth)acrylate compound obtained via esterification reaction can be blended, if necessary, in a range that does not impair the effects of the invention. Specific examples include polyethylene glycol di(meth)acrylate, ethylene glycol di(meth)acrylate, polypropylene glycol di(meth)acrylate, propylene glycol di(meth) acrylate, tetramethylene glycol di(meth)acrylate, polytetramethylene glycol di(meth)acrylate, di(meth)acrylate of a bisphenol A alkylene oxide adduct, di(meth)acrylate of a bisphenol F alkylene oxide adduct, butanediol di(meth) acrylate, hexanediol di(meth)acrylate, and nonanediol di(meth)acrylate.

Examples of a trifunctional or higher functional (meth) acrylate compound include urethane (meth)acrylate which is a reaction product of a compound having hydroxyl groups such as pentaerythritol tri(meth)acrylate and dipentaerythritol penta(meth)acrylate and three or more (meth)acryloyl groups and organic polyisocyanate.

In addition, examples of organic polyisocyanate include hexamethylene diisocyanate, tetra methylene diisocyanate, trimethylhexamethylene diisocyanate, lysine diisocyanate, isophorone diisocyanate, norbornane diisocyanate, tolyl ene diisocyanate hydride, 4,4'-diphenylmethanediisocyanate hydride, xylylene diisocyanate hydride, 4,4'-dicyclohexyl-methanediisocyanate, and hexamethylene diisocyanate trimer.

Further, it is also possible to blend a trifunctional or higher functional (meth)acrylate compound obtained via esterification reaction, if necessary, in a range that does not impair the effects of the invention. Examples thereof include polyol poly(meth)acrylate such as glycerin tri(meth)acrylate, trimethylolpropane tri(meth)acrylate, tri or tetra(meth) acrylate of pentaerythritol, tri or tetra(meth)acrylate of ditrimethylolpropane, or tri, tetra, penta or hexa(meth)acrylate of dipentaerythritol;

poly(meth)acrylate of a polyol alkylene oxide adduct such as tri or tetra(meth)acrylate of a pentaerythritol alkylene oxide adduct, tri or tetra(meth)acrylate of a ditrimethylolpropane alkylene oxide adduct, or tri, tetra, penta or hexa (meth)acrylate of a dipentaerythritol alkylene oxide adduct; and tri(meth)acrylate of an isocyanuric acid alkylene oxide adduct.

Examples of the alkylene oxide adduct described above include an ethylene oxide adduct, a propylene oxide adduct, and an ethylene oxide-propylene oxide adduct.

The content rate of the component (D) is preferably from 0% to 60% by weight include and more preferably 0% to 30% by weight with respect to 100 parts by weight in total of a curable component.

By setting the content rate of the component (D) to not more than 60% by weight, it is possible to prevent a cured film from being breakable in a particular case in which the component (D) is a polyfunctional unsaturated ethylene compound.

2-4. Component (E)

The composition of the invention can include an organic solvent as the component (E) in order to, for example, improve performance of coating on a base material.

Specific examples of the component (E) include: alcohol compounds such as methanol, ethanol, isopropanol and butanol; alkylene glycol monoether compounds such as ethylene glycol monomethylether and propylene glycol monomethylether; acetone alcohol such as die acetone alcohol; aromatic compounds such as benzene, toluene, and xylene; ester compounds such as propylene glycol monomethylether acetate, ethyl acetate, and butyl acetate; ketone compounds such as acetone, methylethylketone, and methylisobutylketone; ether compounds such as dibutylether; and N-methylpyrrolidone.

Of these, alkylene glycol monoether compounds and ketone compounds are preferable, and alkylene glycol monoether compounds are more preferable.

The content rate of the component (E) is preferably from 10 to 1,000 parts by weight, more preferably from 50 to 500 parts by weight, and still more preferably 50 to 300 parts by weight with respect to 100 parts by weight in total of a curable component. When the content rate is within the above range, a composition having have viscosity appropriate for coating can be obtained, and thus, the composition can be readily applied by a publicly known application method described below.

3. Purposes

The composition of the invention can be used for various purposes.

Examples of preferable purposes include a coating composition for hard coating or the like, an ink composition for offset or ink-jet printing or the like, and a pattern formation composition for a photosensitive lithographic printing plate, a color resist, or the like.

Individual compositions are explained below.

3-1. Coating Composition

As the composition of the invention has excellent thin film curing ability and allows a cured product to have high hardness, it can be preferably used as a coating composition.

A coating composition can be preferably used for hard coating. Examples of a base material include plastic films used for polarizer protection films and antireflection films and resin molded products used for home electronics and car interior/exterior parts.

A coating composition contains the above-described (A) as an essential component. However, various components can be blended therewith depending on purposes.

Specific examples of other components include antioxidants, ultraviolet absorbers, colorants/dyes, silane coupling agents, surface modifiers, and polymers as well as the above-described components (B), (C), (D), and (E).

These components are explained below.

As the other components described below, the exemplified compounds may be used singly, or in combination of two or more kinds thereof.

1) Antioxidant

An antioxidant is blended in order to improve durability such as heat resistance, weathering resistance, or the like of a cured film.

Examples of an antioxidant include phenol-based antioxidants, phosphorus-based antioxidants, and sulfur-based antioxidants.

Examples of phenol-based antioxidants include hindered phenols such as di-t-butylhydroxytoluene. Examples of commercially available antioxidants include AO-20, AO-30, AO-40, AO-50, AO-60, AO-70, and AO-80 manufactured by Adeka Corporation.

Examples of phosphorus-based antioxidants include phosphines such as trialkyl phosphine and triaryl phosphine, trialkyl phosphite, and triaryl phosphite. Examples of their derivatives as commercially available products include ADK STAB PEP-4C, PEP-8, PEP-24G PEP-36, HP-10, 260, 522A, 329K, 1178, 1500, 135A, and 3010 manufactured by Adeka Corporation.

Examples of sulfur-based antioxidants include thioether-based compounds. Examples of commercially available products include AO-23, AO-412S, and AO-503A manufactured by Adeka Corporation.

These examples may be used singly, or in combination of two or more kinds thereof. Examples of a preferable combination of these antioxidants include a combination of a phenol-based antioxidant and a phosphorus-based antioxidant and a combination of a phenol-based antioxidant and a sulfur-based antioxidant.

The content rate of an antioxidant can be set depending on purposes, if appropriate. The content rate is preferably from 0.01 to 5 parts by weight and more preferably from 0.1 to 1 parts by weight with respect to 100 parts by weight in total of a curable component.

By setting the content rate to not less than 0.1 parts by weight, durability of a composition can be improved. Meanwhile, by setting the content rate to not more than 5 parts by weight, favorable curing ability and adhesiveness can be achieved.

2) Ultraviolet Absorber

An ultraviolet absorber is blended in order to improve light resistance of a cured film.

Examples of an ultraviolet absorber include triazine-based ultraviolet absorbers such as TINUVIN400, TINUVIN405, TINUVIN460, and TINUVIN479 and benzotriazole-based ultraviolet absorbers such as TINUVIN900, TINUVIN928, and TINUVIN1130 manufactured by BASF SE.

The content rate of an ultraviolet absorber can be set depending on purposes, if appropriate. The content rate is preferably from 0.01 to 5 parts by weight and more preferably from 0.1 to 1 parts by weight with respect to 100 parts by weight in total of a curable component. By setting the content rate to not less than 0.01% by weight, a cured film is allowed to have favorable light resistance. Meanwhile, by setting the content rate to not more than 5% by weight, a composition is allowed to have excellent curing ability.

3) Colorant/Dye

Examples of colorants include organic colorants and inorganic colorants.

Specific examples of organic colorants include: insoluble azo colorants such as toluidine red, toluidine maroon, hansa yellow, benzidine yellow, and pyrazolone red; soluble azo colorants such as lithol red, helio-Bordeaux, pigment scarlet, and permanent red 2B; derivatives from vat dyeing dyes such as alizarin, indanthrone, and thioindigo maroon; phthalocyanine-based organic colorants such as phthalocyanine blue and phthalocyanine green; quinacridone-based organic colorants such as quinacridone red and quinacridone magenta; perylene-based organic colorants such as perylene red and perylene scarlet; isoindolinone-based organic colorants such as isoindolinone yellow and isoindolinone orange; pyranthrone-based organic colorants such as pyranthrone red and pyranthrone orange; thioindigo-based organic colorants; condensed azo-based organic colorants; benzimidazolone-based organic colorants; quinophthalone-based organic colorants such as quinophthalone yellow; isoindoline-based organic colorants such as isoindoline yellow; and other colorants such as flavanthron yellow, acyl amideyellow, nickel azoyellow, copper azomethine yellow, perinone orange, anthrone orange, dianthraquinonylred, and dioxazine violet.

In addition, specific examples of inorganic colorants include oxidized titanium, barium sulfate, calcium carbonate, zinc flower, lead sulfate, yellow lead, zinc yellow, rouge (red iron oxide (III)), cadmium red, ultramarine, iron blue, chromic oxide green, cobalt green, amber, titanium black, and synthetic iron oxide black. Carbon black exemplified as a filler described above can also be used as an inorganic colorant.

Various conventionally known compounds can be used as dyes.

4) Silane Coupling Agent

A silane coupling agent is blended in order to improve force of interfacial adhesion between a cured film and a base material.

A silane coupling agent is not particularly limited as long as it can contribute to adhesion to a base material.

Specific examples of a silane coupling agent include 2-(3,4-epoxy cyclohexyl)ethyltrimethoxysilane, 3-glycidoxypropyltrimethoxysilane, 3-glycidoxypropylmethyldiethoxysilane, 3-glycidoxypropyltriethoxysilane, N-2-(aminoethyl)-3-aminopropylmethyldimethoxysilane, N-2-(aminoethyl)-3-aminopropyltrimethoxysilane, N-2-(aminoethyl)-3-aminopropyltriethoxysilane, 3-aminopropyltrimethoxysilane, 3-aminopropyltriethoxysilane, 3-triethoxysilyl-N-(1,3-dimethyl-butylidene)propylamine, N-phenyl-3-aminopropyltrimethoxysilane, 3-mercaptopropylmethyldimethoxysilane, and 3-mercaptopropyltrimethoxysilane.

The blending rate of a silane coupling agent can be set depending on purposes, if appropriate. The blending rate is preferably from 0.1 to 10 parts by weight and more preferably from 1 to 5 parts by weight with respect to 100 parts by weight in total of a curable component. By setting the blending rate to not less than 0.1 parts by weight, the adhesion force of a composition can be improved. Meanwhile, by setting the blending rate to not more than 10 parts by weight, time-dependent changes in adhesion force can be prevented.

5) Surface Modifier

A surface modifier may be added to the composition of the invention in order to, for example, improve a leveling property upon coating or improve slidability of a cured film to improve abrasion resistance.

Examples of a surface modifier include surface conditioning agents, surfactants, leveling agents, antifoamers, slidability-imparting agents and antifouling property-imparting agents. These publicly known surface modifiers can be used.

Of these, silicone-based surface modifiers and fluorine-based surface modifiers are favorable examples. Specific examples include silicone-based polymers and oligomers having a silicone chain and a polyalkylene oxide chain, silicone-based polymers and oligomers having a silicone chain and a polyester chain, fluorine-based polymers and oligomers having a perfluoroalkyl group and a polyalkylene oxide chain, and fluorine-based polymers and oligomers having a perfluoroalkyl ether chain and a polyalkylene oxide chain.

In addition, in order to, for example, increase ability to maintain slidability, a surface modifier having an unsaturated ethylene group and preferably a (meth)acryloyl group in its molecule may be used.

The content rate of a surface modifier is preferably from 0.01 to 1.0 parts by weight with respect to 100 parts by weight in total of a curable component. Excellent surface smoothness of a coating film can be achieved within the above range.

6) Polymer

The composition of the invention may further contain a polymer in order to, for example, further improve resistance to curling of the obtained cured film.

Examples of a favorable polymer include (meth)acrylic-based polymers. Examples of a monomer having a favorable configuration include methyl(meth)acrylate, cyclohexyl (meth)acrylate, (meth)acrylic acid, glycidyl(meth)acrylate, and N-(2-(meth)acryloxyethyl)tetrahydrophthalimide. In the case of a polymer obtained by copolymerizing (meth)acrylic acid, glycidyl (meth)acrylate may be added, thereby introducing a (meth)acryloyl group into a polymer chain.

The content rate of a polymer is preferably from 0.01 to 10 parts by weight with respect to 100 parts by weight in total of a curable component. Further excellent resistance to curling of the obtained cured film can be achieved within the above range.

3-2. Ink Composition

As the composition of the invention has excellent thin film curing ability, it can be preferably used for transparent overprint varnish ink and yellow, red, indigo, or ink black color printing ink used for printing by a printer after single color or multicolor printing.

Examples of a printing system include various printing systems such as offset printing (usual lithography with the use of dampening water or waterless lithography without the use of dampening water), relief printing (platen press printing, semi-rotary relief printing, rotary printing, intermittent rotary printing, or flexo printing), intaglio printing (gravure printing), stencil printing (screen printing), and ink-jet printing. As the composition of the invention has excellent emulsification stability, the composition can be preferably used for offset printing with the use of dampening water. In addition, as the composition has low viscosity, it can also be preferably used for ink-jet printing.

The ink composition contains the above-described (A) as an essential component. However, various components can be blended therewith depending on purposes.

A method of producing an ink composition may be carried out in accordance with the conventional method of producing an ink composition. In one example of the method, after the component (A), the component (B) (in a case in which the active energy beam is ultraviolet ray), the component (F), the component (G), a polymerization inhibitor, wax, and the other additives are blended, a colorant is added, followed by dispersion by means of a disperser such as a triple role mill or bead mill.

Specific examples of the other components include a binder (hereinafter referred to as "component (F)"), a colorant (hereinafter referred to as "component (G)"), a plasticizer, and an anti-friction agent as well as the components (B), (C), and (D).

These components are explained below.

As the other components, the exemplified compounds may be used singly, or in combination of two or more kinds thereof.

1) Component (F)

Examples of the component (F) in the invention include a diallyl phthalate resin having no polymerizable groups and an epoxy acrylate compound, urethane acrylate, and polyester acrylate each having at least one polymerizable group in its molecule.

Among the binder components described above, diallyl phthalate resins are prepolymers that are synthesized from diallyl phthalate monomers or diallyl isophthalate monomers. There are several commercially available products of different orthophthalic and isoorthophthalic monomers having different molecular weights, which can be used in the invention. Specific examples include DAISO DAP A, DAISO DAP S, DAISO DAP K, and DAISO ISODAP distributed by Daiso Co., Ltd. In consideration of ink cured film intensity, compatibility with the component (A), etc., DAISO DAP A is most preferable among the commercially available products described above.

The content percent of the component (F) in the ink composition is preferably from 10% to 65% by weight with respect to the total amount of ink. When the content percent is less than 10% by weight, sufficient film curing ability and offset printing adequacy cannot be achieved. When the addition amount corresponds to more than 65% by weight, since binders having these polymerizable groups are highly viscous in general, it is difficult to achieve favorable viscosity of offset ink in the composition described in the Examples of the invention.

2) Component (G)

Examples of a colorant as the component (G) include organic colorants and inorganic colorants. Examples of organic colorants include publicly known organic colorants for coloring. Examples of organic colorants that can be used include organic colorants for printing ink listed in "Organic Colorant Handbook (author: Isao Hashimoto; Publisher: Color Office; First edition, 2006)" such as soluble azo colorants, insoluble azo colorants, condensed azo colorants, metalphthalocyanine colorants, metal-free phthalocyanine colorants, quinacridone colorants, perylene colorants, perinone colorants, isoindolinone colorants, isoindoline colorants, dioxazine colorants, thioindigo colorants, anthraquinone-based colorants, quinophthalone colorants, metal complex colorants, diketopyrrole colorants, carbon black colorants, and other polycyclic colorants.

Specific examples of inorganic colorants include oxidized titanium, barium sulfate, calcium carbonate, zinc flower, lead sulfate, yellow lead, zinc yellow, rouge (red iron oxide (III)), cadmium red, ultramarine, chromic oxide green, cobalt green, amber, titanium black, synthetic iron oxide black, and carbon black.

In the invention, inorganic fine particles may be used as extender pigments. Examples of inorganic fine particles include: inorganic coloring pigments such as oxidized titanium, graphite, and zinc flower; inorganic extender pigments of calcium carbonate power, precipitated calcium carbonate, gypsum, clay (china clay), silica powder, diatomaceous earth, talc, kaolin, alumina white, barium sulfate, aluminum stearate, magnesium carbonate, baryta powder, and polishing powder; silicone; and glass beads.

By using these inorganic fine particles in ink at from 0.1% to 20% by weight, effects of, for example, adjusting ink fluidity, preventing misting, and preventing permeation into a printing base material such as paper can be obtained.

3) Plasticizer and Anti-Friction Agent

As plasticizers and anti-friction agents, wax compounds such as paraffin wax, carnauba wax, beeswax, microcrystalline wax, polyethylene wax, oxidized polyethylene wax, polytetrafluoroethylene wax, and amide wax, fatty acids having about 8 to 18 carbon atoms such as coconut oil fatty acid and soybean oil fatty acid, and the like can be blended and used in a range that does not impair the effects of the invention.

3-3. Pattern Formation Composition

The composition of the invention has high exposure sensitivity, which is significantly excellent in developability, and allows fine and precise pattern formation. Therefore, the composition can be preferably used as a pattern formation composition.

The pattern formation composition contains the above-described (A) as an essential component. However, various components can be blended therewith depending on purposes. Specific examples of the other components include an alkali-soluble resin (hereinafter referred to as "component (H)") as well as the components (B), (D), and (E), antioxidants, ultraviolet absorbers, silane coupling agents, and surface modifiers described above. The component (H) is explained below.

As the other components, the exemplified compounds may be used singly, or in combination of two or more kinds thereof.

1) Component (H)

The component (H) in the invention is not particularly limited as long as it acts as a binder on the component (A) and is soluble in a developer and particularly preferably in an alkali developer used in the development process.

Examples of the component (H) include addition polymers, polyesters, epoxy resins, and polyethers. Addition polymers obtained by polymerizing unsaturated ethylene monomers are preferable.

As the component (H), an alkali-soluble resin having carboxyl groups is preferable. A copolymer (hereinafter referred to as "carboxyl group-containing copolymer") of an unsaturated ethylene monomer (hereinafter referred to as "carboxyl group-containing unsaturated monomer") having at least one carboxyl group and an unsaturated ethylene monomer that can be copolymerized therewith (hereinafter referred to as "copolymerizable unsaturated monomer") is particularly preferable.

Examples of carboxyl a group-containing unsaturated monomer include: unsaturated monocarboxylic acids such as (meth)acrylic acid, crotonic acid, α-chloracrylic acid, and cinnamic acid; unsaturated dicarboxylic acids or anhydrides thereof such as maleic acid, maleic anhydride, fumaric acid, itaconic acid, itaconic anhydride, citraconic acid, citraconic anhydride, and mesaconic acid; trivalent or higher valent unsaturated polycarboxylic acids or anhydrides thereof; mono((meth)acryloyloxyalkyl)esters of divalent or higher valent polycarboxylic acids such as mono(2-(meth)acryloyloxyethyl) succinate and mono(2-(meth)acryloyloxyethyl) phthalate; and mono(meth)acrylates of polymers having a carboxy group and a hydroxyl group at both terminals such as ω-carboxy-polycaprolactone mono(meth)acrylate. Of these carboxyl group-containing unsaturated monomers, mono(2-acryloyloxyethyl) succinate and mono(2-acryloyloxyethyl) phthalate are commercially available under the trade names of ARONIX M-5300 and M-5400 (Toagosei Co., Ltd.), respectively.

Carboxyl group-containing unsaturated monomers may be used singly, or in mixture of two or more kinds thereof.

In addition, a copolymerizable unsaturated monomer may be a monomer that is copolymerized with a carboxyl group-containing unsaturated monomer. Aromatic vinyl compounds, unsaturated carboxylic acid esters, unsaturated imides, and macromonomers having mono(meth)acryloyl groups at their ends, and the like are preferable.

Examples of aromatic vinyl compounds include styrene, α-methylstyrene, o-vinyltoluene, m-vinyltoluene, p-vinyltoluene, p-chlorostyrene, o-methoxystyrene, m-methoxystyrene, p-methoxystyrene, 2-vinylbenzylmethylether, 3-vinylbenzylmethylether, 4-vinylbenzylmethylether, 2-vinylbenzylglycidyl ether, 3-vinylbenzylglycidyl ether, and 4-vinylbenzylglycidyl ether.

Examples of unsaturated carboxylic acid esters include methyl(meth)acrylate, ethyl(meth)acrylate, n-propyl(meth)acrylate, isopropyl(meth)acrylate, n-butyl(meth)acrylate, isobutyl(meth)acrylate, sec-butyl(meth)acrylate, t-butyl (meth)acrylate, 2-hydroxyethyl(meth)acrylate, 2-hydroxypropyl(meth)acrylate, 3-hydroxypropyl(meth)acrylate, 2-hydroxybutyl(meth)acrylate, 3-hydroxybutyl(meth)acrylate, 4-hydroxybutyl(meth)acrylate, allyl(meth)acrylate, benzyl(meth)acrylate, cyclohexyl(meth)acrylate, phenyl (meth)acrylate, 2-methoxyethyl(meth)acrylate, 2-phenoxyethyl(meth)acrylate, methoxydiethylene glycol(meth)acrylate, methoxytriethylene glycol(meth)acrylate, methoxypropylene glycol(meth)acrylate, methoxydipropylene glycol(meth)acrylate, isobornyl(meth)acrylate, tricyclo[5.2.1.0$^{2,6}$]decane-8-yl(meth)acrylate, 2-hydroxy-3-phenoxypropyl(meth)acrylate, and glycerol mono(meth)acrylate.

Examples of unsaturated imides include maleimide, N-phenylmaleimide, and N-cyclohexylmaleimide.

Examples of macromonomers having mono(meth)acryloyl groups at their ends include macromonomers having polymer molecular chains of polystyrene, polymethyl(meth)acrylate, poly-n-butyl(meth)acrylate, polysiloxane, and the like.

In addition to the above, examples of copolymerizable unsaturated monomers include: imide (meth)acrylates such as 2-(3,4,5,6-tetrahydrophthalimide)ethyl(meth)acrylate, and 2-(2,3-dimethylmaleimide)ethyl(meth)acrylate; unsaturated carboxylic acid amino alkyl esters such as 2-aminoethyl(meth)acrylate, 2-dimethylaminoethyl(meth)acrylate, 2-aminopropyl(meth)acrylate, 2-dimethylaminopropylacrylate, 3-aminopropyl(meth)acrylate, and 3-dimethylaminopropyl(meth)acrylate; unsaturated carboxylic acid glycidyl esters such as glycidyl (meth)acrylate; indenes such as indene and 1-methylindene; carboxylic acid vinyl esters such as vinyl acetate, vinyl propionate, vinyl butyrate, and vinyl benzoate; unsaturated ethers such as vinyl methyl ether, vinyl ethyl ether, and allyl glycidyl ether; vinyl cyanide compounds such as (meth)acrylonitrile, α-chloroacrylonitrile, and vinylidene cyanide; unsaturated amides such as (meth)acrylamide, α-chloroacrylamide, and N-2-hydroxyethyl(meth)acrylamide; and aliphatic conjugated dienes such as 1,3-butadiene, isoprene, and chloroprene.

These copolymerizable unsaturated monomers may be used singly, or in mixture of two or more kinds thereof.

As a carboxyl group-containing copolymer, a copolymer of a carboxyl group-containing unsaturated monomer component containing (meth)acrylic acid as an essential component and optionally further containing at least one compound selected from the group consisting of succinic acid mono(2-(meth)acryloyloxyethyl) and ω-carboxy-polycaprolactone mono(meth)acrylate and at least one selected from the group consisting of styrene, methyl(meth)acrylate, 2-hydroxyethyl(meth)acrylate, allyl(meth)acrylate, benzyl(meth)

acrylate, glycerol mono(meth)acrylate, N-phenylmaleimide, a polystyrene macromonomer, and a polymethylmethacrylate macromonomer (hereinafter referred to as "carboxyl group-containing copolymer (a)") is preferable.

Specific examples of a carboxyl group-containing copolymer (a) include a (meth)acrylic acid/methyl(meth)acrylate copolymer, a (meth)acrylic acid/benzyl(meth)acrylate copolymer, a (meth)acrylic acid/2-hydroxyethyl(meth)acrylate/benzyl(meth)acrylate copolymer, a (meth)acrylic acid/glycidyl (meth)acrylate copolymer, a (meth)acrylic acid/glycidyl (meth)acrylate/styrene copolymer, a (meth)acrylic acid/methyl(meth)acrylate/polystyrene macromonomer copolymer, a (meth)acrylic acid/methyl(meth)acrylate/polymethylmethacrylate macromonomer copolymer, a (meth)acrylic acid/benzyl(meth)acrylate/polystyrene macromonomer copolymer, a (meth)acrylic acid/benzyl(meth)acrylate/polymethylmethacrylate macromonomer copolymer, a (meth)acrylic acid/2-hydroxyethyl(meth)acrylate/benzyl(meth)acrylate/polystyrene macromonomer copolymer, a (meth)acrylic acid/2-hydroxyethyl(meth)acrylate/benzyl(meth)acrylate/polymethylmethacrylate macromonomer copolymer, a methacrylic acid/styrene/benzyl(meth)acrylate/N-phenylmaleimide copolymer, a (meth)acrylic acid/succinic acid mono[2-(meth)acryloyloxyethyl]/styrene/benzyl(meth)acrylate/N-phenylmaleimide copolymer, a (meth)acrylic acid/succinic acid mono[2-(meth)acryloyloxyethyl]/styrene/allyl(meth)acrylate/N-phenylmaleimide copolymer, (meth)acrylic acid/styrene/benzyl(meth)acrylate/glycerol mono(meth)acrylate/N-phenylmaleimide copolymer, and a (meth)acrylic acid/ω-carboxy-polycaprolactone mono(meth)acrylate/styrene/benzyl(meth)acrylate/glycerol mono(meth)acrylate/N-phenylmaleimide copolymer.

The copolymerization rate of a carboxyl group-containing unsaturated monomer in a carboxyl group-containing copolymer is usually from 5 to 50% by weight and preferably from 10 to 40% by weight. In this case, by setting the copolymerization rate to not less than 5% by weight, solubility of the obtained composition in an alkali developer can be improved.

Meanwhile, by setting the copolymerization rate to not more than 50% by weight, solubility in an alkali developer can be optimized, thereby making it possible to prevent detachment of a spacer layer or pixels from a substrate and film roughening of a spacer surface upon image development with an alkali developer.

As the component (H) in the invention, an alkali-soluble resin having an unsaturated ethylene group as a side chain is preferable in that the crosslinking density of the obtained cured film, coating film strength, heat resistance, and chemical resistance are improved.

As an alkali-soluble resin having an unsaturated ethylene group as a side chain, an alkali-soluble resin having a carboxyl group is preferable. Examples of such resin include a resin obtained by adding an unsaturated compound having an epoxy group (hereinafter referred to as "unsaturated epoxy compound") to the carboxyl group-containing copolymer described above.

Examples of an unsaturated epoxy compound include epoxy group-containing (meth)acrylates such as glycidyl (meth)acrylate and cyclohexene oxide-containing (meth)acrylate.

A method of additional reaction may be carried out in accordance with an ordinary method. The component (H) can be produced by adding an unsaturated epoxy compound to a carboxyl group-containing copolymer in an organic solvent or in a solvent-free system. As additional reaction conditions, the reaction temperature, reaction time, and a catalyst may be selected depending on an individual reaction, if appropriate.

Mw of the component (H) is preferably from 3,000 to 300,000 and more preferably from 5,000 to 100,000. In addition, the number average molecular weight (hereinafter referred to as "Mn") is preferably from 3,000 to 60,000 and more preferably from 5,000 to 25,000. In addition, Mw and Mn in the invention refer to values calculated via polystyrene conversion of the molecular weight measured by GPC (elution solvent: tetrahydrofuran).

In the invention, by using the component (H) having such specific Mw and Mn, a photosensitive resin composition having excellent developability can be obtained, thereby making it possible to form a pattern having sharp pattern edges. In addition, upon image development, residues, scumming, film remainders, and the like are unlikely to occur on an unexposed portion of a substrate and a light-blocking layer. The ratio of Mw to Mn (Mw/Mn) of the component (H) is usually from 1 to 5 and preferably from 1 to 4.

The component (H) may be used singly, or in combination of two or more kinds thereof.

The proportion of the component (A) is preferably from 10 to 100% by weight and more preferably from 20 to 100% by weight and the proportion of the component (H) is preferably from 0 to 90% by weight and more preferably from 0 to 80% by weight with reference to the total amount of the components (A) and (H). When the proportion of the component (H) is less than 10% by weight, it results in a decrease in crosslinking density, which tends to cause reduction of coating film strength, heat resistance, and chemical resistance.

The proportion of the components (A) and (H) in the composition is preferably from 10 to 50% by weight in terms of the total amount of the components (A) and (H). By setting the proportion to not less than 10% by weight, thinning of film thickness after prebake can be prevented. Meanwhile, by setting the proportion to not more than 50% by weight, appropriate viscosity of the composition can be achieved, thereby making it possible to prevent poor coating performance and an increase in film thickness after prebake.

4. Using Method 4-1. Method of Using Coating Composition

A method of using the composition of the invention can be carried out in accordance with an ordinary method.

For example, a method wherein after the composition is applied to a base material, active energy beam irradiation or heating is conducted to cure the composition.

Specifically, after the composition is applied to a base material of interest by a usual painting method, in the case of an active energy beam-curable composition, a method of curing by active energy beam irradiation is employed, and in the case of a thermosetting composition, a method of curing by heating is employed. When the composition is used for a molding material or the like, after the composition is injected into a certain mold form, for example, a method of curing by active energy beam irradiation is employed in the case of an active energy beam-curable composition, and a method of curing by heating is employed in the case of a thermosetting composition.

As a method of an active energy beam irradiation, a usual method known as a conventional curing method can be employed.

In addition, it is also possible to employ a method wherein the composition mixed with the component (C) (photopolymerization initiator) and the component (D) (thermal polymerization initiator) used in combination is irradiated with an active energy beam, followed by heating for curing, thereby improving adhesion to a base material.

Base materials to which the composition of the invention can be applied include various materials such as plastic, wood, metal, inorganic material, and paper.

Specific examples of plastics include cellulose acetate resins such as polyvinyl alcohol, triacetyl cellulose, and diacetyl cellulose, acrylic resins, cyclic polyolefin resins including, as monomers, cyclic olefins such as polyethylene terephthalate, polycarbonate, polyarylate, polyethersulfone, and norbornene, polyvinyl chloride, epoxy resins, and polyurethane resins.

Examples of wood include natural wood and synthetic wood.

Examples of metals include metals such as steel plate, aluminum, and chromium, and metal oxides of oxidized zinc (ZnO), indium tin oxide (ITO), and the like.

Examples of inorganic materials include glass, mortar, concrete, and stone material.

Of these, plastic base material is particularly preferable.

Film thickness of a cured film of the composition on a base material may be determined depending on purposes, if appropriate. Thickness of a cured film may be selected depending on the application of a base material to be used or a base material having the produced cured film. However, the film thickness is preferably from 1 to 500 μm and more preferably from 5 to 200 μm.

A method of applying the composition of the invention by coating to a base material may be determined depending on purposes, if appropriate. Examples thereof include methods of coating by a bar coater, an applicator, a doctor blade, a dip coater, a role coater, a spin coater, a flow coater, a knife coater, a comma coater, a reverse role coater, a die coater, a lip coater, a gravure coater, a microgravure coater, and an ink-jet system.

Examples of an active energy beam for curing the composition of the invention include ultraviolet ray, visible ray, and an electron beam. Ultraviolet ray is preferable.

Examples of an ultraviolet ray irradiation device include high-pressure mercury lamps, metal halide lamps, ultraviolet ray (UV) electrodeless lamps, and light-emitting diodes (LEDs).

Irradiation energy may be determined depending on type of active energy beam and the blending composition, if appropriate. In one example of the use of a high-pressure mercury lamp, irradiation energy in the UV-A range is preferably from 100 to 5,000 mJ/cm$^2$ and more preferably from 200 to 1,000 mJ/cm$^2$.

4-2. Method of Using Ink Composition

A printing base material used for a printed material of the invention is not particularly limited. Examples thereof include papers such as high-quality paper, coated paper, art paper, imitation paper, thin paper, and heavy paper, various synthetic papers, films or sheets of polyester resins, acrylic resins, vinyl chloride resins, vinylidene chloride resins, polyvinyl alcohol, polyethylene, polypropylene, polyacrylonitrile, ethylene vinyl acetate copolymers, ethylene vinyl alcohol copolymers, ethylene methacrylic acid copolymers, nylon, polylactate, and polycarbonate, cellophane, aluminum foil, and other various base materials used as conventional printing base materials.

Of these, paper base materials are particularly preferable.

Film thickness of a cured film of the composition on a base material may be determined depending on purposes, if appropriate. Thickness of a cured film may be selected depending on the application of a base material to be used or a base material having the produced cured film. However, the thickness is preferably from 1 to 20 μm and more preferably from 1 to 10 μm.

In a case in which the composition of the invention is used for offset ink, an offset printer for continuous supplying water on a printing plate can be preferably used in a method of coating on a base material. In addition, a sheet-fed offset printer using sheet-form printing paper and an offset rotary press using reel-form printing paper can be favorably used in any paper supply system.

In a case in which the composition of the invention is used for ink-jet ink, a publicly known ink-jet recording device for forming an image ejected by an ink-jet system can be favorably used in a method of coating on a base material.

In consideration of ejecting performance of the ink-jet system, viscosity of the composition is preferably from 7 mPa·s to 30 mPa·s and more preferably from 7 mPa·s to 20 mPa·s at the ejecting temperature (e.g., from 40° C. to 80° C. and preferably from 25° C. to 30° C.).

Examples of an active energy beam for curing the composition of the invention include ultraviolet ray, visible ray, and an electron beam. Ultraviolet ray is preferable. An ultraviolet ray irradiation device may be similar to the device described above.

Irradiation energy can be determined depending on type of active energy beam and the blending composition, if appropriate. Irradiation energy may be similar to the irradiation energy described above.

4-3. Method of Using Composition for Pattern Formation

Examples of a pattern formation composition include coloring compositions for forming photosensitive lithographic printing plates, resists such as etching resists and solder resists, columnar spacers for liquid crystal panel production, and pixels and black matrix in color filters, and color filter protection films.

The composition of the invention can be more preferably used for coloring compositions for columnar spacers and color filters and color filter protection films used in liquid crystal panel production.

In a case in which the composition of the invention is used for columnar spacers and color filter protection films, in order to improve coating performance and developability, a nonionic surfactant such as polyoxyethylene lauryl ether and a fluorine-based surfactant can be added to the composition. In addition, if necessary, an adhesive aid, a preservation stabilizer, and an antifoamer may be optionally added.

The applications of a columnar spacer (hereinafter simply referred to as "spacer") and a coloring composition are explained below.

4-3-1. Spacer

A spacer is formed with a photo-curable coating film of the composition by a photolithography method. The spacer can be formed in any size at a given site on a liquid crystal panel substrate. Usually, the spacer is often formed on a black matrix area serving as a light-blocking part of a color filter or on a TFT electrode.

A method of forming a spacer can be carried out in accordance with an ordinary method. One example is a method wherein a spacer is formed by applying the composition of the invention on a substrate of glass or the like to result in a film thickness necessary for cell gap configuration, heating (hereinafter referred to as "prebake") and then drying a coating film, and carrying out steps of exposure, image development, and post-heating (hereinafter referred to as "postbake").

When the composition is applied on a substrate, in consideration of image development and film reduction or deformation due to postbake or the like, the composition is applied such that the resulting coat becomes slightly thicker than a designed cell gap value. Specifically, it is preferable to achieve a film thickness of preferably from 5 to 10 μm and more preferably from 6 to 7 μm after prebake.

Examples of a coating method include a printing method, a spray method, a role coating method, a bar coating method, a curtain coating method, a spin coating method, and a die coating method (slit coating method). Usually, a spin coating method or a die coating method is employed.

After the composition is applied to a substrate, prebake is conducted. In this case, the temperature and time are set to from 50° C. to 150° C. and from 5 to 15 minutes or thereabouts.

The coating film after prebake is irradiated with light via a mask having a certain pattern shape for forming a spacer.

Light used is preferably ultraviolet ray or visible ray. Light with a wavelength of from 240 nm to 410 nm obtained by a high-pressure mercury lamp, a metal halide lamp, or the like is used.

Light irradiation conditions are determined depending on types of light sources, an absorption wavelength of a photopolymerization initiator to be used, film thickness of a coating film, or the like. The light irradiation dose is preferably approximately from 50 to 600 mJ/cm². When the light irradiation dose is smaller than 50 mJ/cm², it causes poor curing, which facilitates detachment of exposed portions upon image development. Meanwhile, when the light irradiation dose is larger than 600 mJ/cm², a fine spacer pattern is unlikely to be obtained.

After light irradiation on the coating film, unexposed portions are removed by a developer.

As a developer, an aqueous solution of an alkali compound can be used. Examples of an alkaline compound include potassium hydroxide, sodium hydroxide, sodium carbonate, sodium hydrogen carbonate, sodium silicate, ammonia, and tetramethylammonium hydroxide. In addition, in order to promote the image development rate, water-soluble organic solvents such as methanol, ethanol, isopropanol, and benzylalcohol and various surfactants may be added in appropriate amounts to a developer.

An image development method may be any of a developer application method, a dipping method, a spray method, and the like. After image development, pattern portions are washed with water for from 0.5 to 1.5 minutes, thereby obtaining a spacer pattern by air drying with compressed air or the like.

The obtained spacer pattern is treated by postbake with a heating device such as a hot plate, an oven, or the like at from 150° C. to 350° C., thereby obtaining a liquid crystal panel spacer in the invention.

By performing postbake, a residual solvent or moisture absorbed during image development can be evaporated, and heat resistance of the spacer can be improved. Although the film thickness of the spacer differs depending on the cell gap value set for a liquid crystal panel, the film thickness is designed to be approximately from 3 to 5 μm after postbake.

4-3-2. Coloring Composition

In a case in which the composition of the invention is used as a coloring composition, a colorant and a colorant dispersant are further blended. These components are explained below.

The colorant is not particularly limited. Various organic or inorganic colorants can be used.

Specific examples of an organic colorant include, in addition to those described above, compounds classified as pigments in the Colour Index (C.I.; published by the Society of Dyers and Colourists), i.e., those with the following color index (C.I.) numbers: yellow-based pigments such as C.I. Pigment Yellow 1, C.I. Pigment Yellow 3, C.I. Pigment Yellow 12, C.I. Pigment Yellow 13, C.I. Pigment Yellow 83, C.I. Pigment Yellow 138, C.I. Pigment Yellow 139, C.I. Pigment Yellow 150, C.I. Pigment Yellow 180, and C.I. Pigment Yellow 185; red-based pigments such as C.I. Pigment Red 1, C.I. Pigment Red 2, C.I. Pigment Red 3, C.I. Pigment Red 177, and C.I. Pigment Red 254; blue-based pigments such as C.I. Pigment Blue 15, C.I. Pigment Blue 15:3, C.I. Pigment Blue 15:4, and C.I. Pigment Blue 15:6; green-based pigments such as C.I. Pigment Green 7 and C.I. Pigment Green 36; C.I. Pigment Violet 23; and C.I. Pigment Violet 23:19.

In addition, a high-intensity G colorant of phthalocyanine with a high bromination rate, which has been conventionally difficult to disperse, e.g., MONASTRAL GREEN 6YC, 9YC (manufactured by Avecia Co., Ltd.), a high color purity G colorant including a metal phthalocyanine colorant with a core metal other than copper such as Mg, Al, Si, Ti, V, Mn, Fe, Co, Ni, Zn, Ge, or Sn, or the like can be used.

Specific examples of inorganic colorants include those similar to the inorganic colorants described above.

In the invention, the colorants may be used singly, or in mixture of two or more kinds thereof.

Colorant dispersion liquid can impart excellent dispersibility to a variety of colorants widely used for color filters of liquid crystal display devices among the above colorants. Specifically, at least one selected from the group consisting of C.I. Pigment Yellow 150, C.I. Pigment Green 36, C.I. Pigment Green 7, C.I. Pigment Yellow 138 C.I. Pigment Yellow 83, C.I. Pigment Blue 15:6, C.I. Pigment Violet 23, C.I. Pigment Red 177, C.I. Pigment Red 254 and, C.I. Pigment Yellow 139, any phthalocyanine colorant having a high bromination rate described above, and any different metalphthalocyanine colorant described above can be favorably used for preparing colorant dispersion liquid.

A colorant dispersant is not particularly limited. Various colorant dispersants can be used.

Specific examples of colorant dispersants that can be used include: amide compounds such as nonanamide, decaneamide, dodecanamide, N-dodecylhexaamide, N-octadecylpropionamide, N,N-dimethyldodecanamide, and N,N-dihexylacetamide; amine compounds such as diethylamine, diheptylamine, dibutylhexadecylamine, N,N,N',N'-tetramethylmethanamine, triethylamine, tributylamine, and trioctylamine; and amines having hydroxy groups such as monoethanolamine, diethanolamine, triethanolamine, N,N,N',N'-(tetra hydroxyethyl)-1,2-diaminoethane, N,N,N'-tri(hydroxyethyl)-1,2-diaminoethane, N,N,N',N'-tetra(hydroxyethylpolyoxyethylene)-1,2-diaminoethane, 1,4-bis(2-hydroxyethyl)piperazine, and 1-(2-hydroxyethyl)piperazine. Other examples include compounds such as nipecotamide, isonipecotamide, and nicotinamide.

Further examples thereof include: (co)polymers of unsaturated carboxylic acid ester such as polyacrylic acid ester; (partial) amine salts, (partial) ammonium salts, and (partial) alkyl amine salts of (co)polymers of unsaturated carboxylic acid ester such as polyacrylic acid; (co)polymers of hydroxyl group-containing unsaturated carboxylic acid ester such as hydroxyl group-containing polyacrylic acid ester or denatured products thereof; polyurethanes; unsaturated polyamides; polysiloxanes; long-chain polyaminoamide phosphates; amides obtained via reaction of poly(lower alkylene imine) and free carboxyl group-containing polyester and salts thereof.

In addition, examples of dispersants as commercially available products include SHIGENOX-105 (trade name, manufactured by Hakkol Chemical Co., Ltd.), DISPER-BYK-101, 130, 140, 170, 171, 182, and 2001 (manufactured by BYK-Chemie Japan K.K.), EFKA-49, 4010, and 9009 (manufactured by EFKA CHEMICALS), SOLSPERSE 12000, 13240, 13940, 17000, 20000, 24000GR, 24000SC, 27000, 28000, and 33500 (manufactured by AstraZeneca K.K.), and PB821 and 822 (manufactured by Ajinomoto Co., Inc.).

The proportion of a colorant dispersant used is preferably from 10 to 90 parts by weight and more preferably from 20 to 80 parts by weight with respect to 100 parts by weight of a colorant.

A coloring composition may be further blended with an ultraviolet ray blocker, an ultraviolet absorber, a surface conditioning agent (leveling agent), and other components, if necessary.

A coloring composition may be produced by directly mixing the component (A), a colorant, a colorant dispersant, and if necessary, other components with the component (E) (organic solvent) and dispersing the mixture using a publicly known disperser. However, in some cases, dispersion of the colorant may become insufficient. Therefore, a method wherein a colorant dispersion liquid is preliminarily prepared is preferable.

According to this method, a photosensitive coloring composition having excellent colorant dispersibility can be readily obtained. In this method, in a particular case in which the component (F) (binder) is blended, a colorant dispersion liquid is preliminarily prepared by mixing or dispersing the component (F) in a solvent for dispersion (hereinafter referred to as "dispersion solvent") of a colorant, a colorant dispersant, and if necessary, a part of the component (F). Separately, a clear resist liquid is prepared by mixing the component (A), and if necessary, the component (F) or other components in a solvent for dilution (hereinafter referred to as "diluting solvent") to dissolve or disperse them. In addition, by mixing the obtained colorant dispersion liquid and the clear resist liquid, and if necessary, conducting dispersion treatment, a coloring composition having excellent colorant dispersibility can be readily obtained. According to this method, a dispersion solvent and a diluting solvent can be independently selected, thereby expanding the range of choice of solvents.

In a case in which a colorant dispersion liquid is not preliminarily prepared, at first, a colorant, a colorant dispersant, and if necessary, an alkali-soluble resin are added to an organic solvent, the mixture is sufficiently mixed and stirred to disperse a colorant, and then the remaining components such as carboxyl group-containing polyfunctional acrylate are added, followed by mixing. Accordingly, inhibition of colorant dispersibility by other blending components can be prevented in the colorant dispersion step, and excellent stability can be achieved.

The thus obtained coloring composition is applied to a support to form a coating film. After drying, the coating film is irradiated with a beam in a certain pattern, thereby partially curing the coating film in a selective manner. Then, after image development with an alkaline liquid, postbake is performed, and thermal curing is further performed. Accordingly, a coloring coating film having a certain pattern can be obtained.

Light to be used is preferably ultraviolet ray or visible ray. Light with a wavelength of 240 nm to 410 nm obtained by a high-pressure mercury lamp, a metal halide lamp, or the like is used. Irradiation energy necessary for curing is usually from about 10 to 500 mJ/cm$^2$. In the exposure step, by irradiating the surface of a coating film with a laser beam or a beam via a mask, a certain site of a coating film can be selectively exposed or cured.

In addition, thermal curing is usually carried out by drying at from 50° C. to 200° C. using a vacuum dryer, an oven, a hot plate, or a different device capable of imparting heat and then performing heating at about 120° C. to 250° C. for curing.

A cured portion in a coating film has a structure in which a colorant is uniformly dispersed in a matrix formed with a network of crosslinking bonds formed via light curing reaction and thermal curing reaction according to the invention described above.

This coloring composition has excellent curing ability, and sufficient curing takes place in a uniform manner through the inside of the composition as a result of an increase in the crosslinking density. Accordingly, an inverse tapered pattern is unlikely to be formed, and a normal tapered pattern having sharp edges and favorable surface smoothness can be formed upon image development.

In addition, since the coloring composition of the invention is sufficiently cured through the inside thereof and thus impurities are trapped in the matrix with a high crosslinking density and hardly eluted into a liquid crystal layer, a colored cured film with high electric reliability can be obtained. In a particular case in which a coloring layer of a liquid crystal panel is prepared using the coloring composition, it is possible to stably maintain voltage in a display, thereby achieving high electric reliability.

Further, the coloring composition allows a highly concentrated colorant to be finely and uniformly dispersed. Therefore, the coloring composition has high colorability and thus can form a coloring pattern with a high coloring concentration even when it is thinly applied, thereby achieving a large color reproduction range.

The coloring composition can be used for forming various coloring coating films. In particular, it is suitable for forming a coloring layer that constitutes the details of a color filter, i.e., pixels or a black matrix.

EXAMPLES

The invention is described in more detail below with reference to the Examples and Comparative Examples.

Note that the term "part(s)" hereinafter used refers to "part(s) by weight."

1. Production Example

1) Production Example 1 (Production of DPHA by a Transesterification Method)

Into a 1-L flask equipped with a stirrer, a thermometer, a gas introducing tube, a rectifier, and a cooling tube, 86.33 parts (0.34 mol) of dipentaerythritol, 690.05 parts (5.30 mol) of 2-methoxyethylacrylate, 4.08 parts (0.04 mol) of DABCO as the catalyst X, 6.52 parts (0.04 mol) of zinc acetate as the catalyst Y, and 1.63 parts (2061 wt ppm with respect to the total weight of the introduced starting materials) of hydroquinone monomethylether were introduced. The obtained liquid was bubbled with an oxygen-containing gas (5% by volume of oxygen, 95% by volume of nitrogen).

While the liquid was stirred during heating at a reaction solution temperature of from 120° C. to 145° C., the pressure in the reaction system was adjusted to from 250 to 760 mmHg, thereby discharging a liquid mixture of 2-methoxyethanol obtained as by-products and 2-methoxyethyl acrylate with progress in transesterification reaction via the rectifier and the cooling tube from the reaction system. In addition, 2-methoxyethyl acrylate was added to the reaction system in an amount equivalent to the number of parts by weight of the discharged liquid, as needed. The pressure in the reaction system was adjusted back to ordinary pressure 24 hours after the start of heating and stirring to finish discharging the liquid mixture.

The reaction solution was cooled to room temperature and the precipitate was separated by filtration. Thereafter, 4.0 parts of aluminum silicate (KYOWAAD 700 (trade name) manufactured by Kyowa Chemical Industry Co., Ltd.) and 4.5 parts of activated carbon (TAIKO S (trade name) manufactured by Futamura Chemical Co., Ltd.) were added to the filtrate. Reduced-pressure distillation was performed at from 70° C. to 95° C. and from 0.001 to 100 mmHg for 8 hours while the filtrate was bubbled with dry air. The distilled liquid including unreacted 2-methoxyethylacrylate was separated. Pressurized filtration was performed by adding 2.0 parts of diatomaceous earth (RADIOLITE (trade name) manufactured by Showa Chemical Industry Co., Ltd.) to the tank liquid. The obtained filtrate was designated as a purified product.

Composition analysis of the purified product was conducted using a high-performance liquid chromatograph equipped with a UV detector. As a result, the purified product was confirmed to include dipentaerythritol pentaacrylate and dipentaerythritol hexaacrylate as main components (hereinafter referred to as "EX-DPHA1"). The yield of the purified product was 89%. The hydroxyl valence of the obtained purified product was measured in accordance with the following method. As a result, it was 15 mg KOH/g. Table 1 shows the results.

Method of Measuring the Valence of Hydroxyl Groups

An acetylation reagent is added to a sample, followed by heating treatment in a warm bath. After natural cooling, acid titration is performed with a potassium hydroxide ethanol solution using a phenolphthalein solution as an indicator in order to obtain the hydroxyl valence.

2) Production Examples 2 and 3 (Production of Polyfunctional Acrylate by a Transesterification Method)

Polyfunctional acrylate was produced in accordance with the method described in Production Example 1 except that the compounds listed in Table 1 were used as polyalcohols and the catalysts X and Y. Table 1 shows the results.

3) Comparative Production Example 1 (Production of Polyfunctional Acrylate by a Transesterification Method)

Polyfunctional acrylate was produced in accordance with the method described in Production Example 1 except that the compounds listed in Table 2 were used as a polyalcohol and the catalysts X and Y. Table 2 shows the results.

TABLE 2

| Comparative Production Example | Abbreviation | Polyalcohol | Catalyst X | Catalyst Y | Purification yield (%) | Hydroxyl valence (mg KOH/g) |
| --- | --- | --- | --- | --- | --- | --- |
| 1 | EX-PETTA2 | Pentaerythritol | Triphenylphosphine | Zinc acetate | 91 | 12 |

4) Comparative Production Example 2 (Production of DPHA by a Dehydration Esterification Method)

Into a flask equipped with a stirrer, a thermometer, a gas introducing tube, a rectifier, a cooling tube, and a water separator, 3,811 parts (15 mol) of dipentaerythritol, 8,425 parts (117 mol) of acrylic acid, 11,111 parts of toluene, 500 parts of p-toluenesulfonic acid, and 18.5 parts (775 wt ppm with respect to the total weight of the introduced starting materials) of copper(II) chloride were introduced. The obtained liquid was bubbled with an oxygen-containing gas (5% by volume of oxygen, 95% by volume of nitrogen).

While the liquid was stirred during heating reflux at 600 mmHg in the reaction system, 1,506 parts (84 mol) of water obtained as a by-product with progress in dehydration esterification reaction was discharged via the rectifier and the cooling tube from the reaction system. Heating of the reaction solution was terminated 7 hours after the start of heating and stirring, and the pressure in the reaction system was adjusted back to ordinary pressure to finish discharging the water.

After the reaction solution was cooled to room temperature, 2,950 parts of water was added and stirred. Then, the reaction solution was allowed to stand still such that the lower layer (aqueous layer) was separated. Thereafter, 2,756 parts of a 20% sodium hydroxide aqueous solution was added to the upper layer (organic layer). The solution was stirred and then allowed to stand still such that the lower layer (aqueous layer) was separated. Subsequently, 2,950 parts of water was added to the upper layer (organic layer). The solution was stirred and then allowed to stand still such that the lower layer (aqueous layer) was separated. To the upper layer (organic layer), 3.6 parts of hydroquinone monomethylether was added. Reduced-pressure distillation was performed at from 60° C. to 90° C. and from 0.001 to

TABLE 1

| Production Example | Abbreviation | Polyalcohol | Catalyst X | Catalyst Y | Purification yield (%) | Hydroxyl valence (mg KOH/g) |
| --- | --- | --- | --- | --- | --- | --- |
| 1 | EX-DPHA1 | Dipentaerythritol | DABCO | Zinc acetate | 89 | 15 |
| 2 | EX-DPHA2 | Dipentaerythritol | DMAP | Zinc Acetylacetonate | 88 | 17 |
| 3 | EX-PETTA1 | Pentaerythritol | N-methylimidazole | Zinc acrylate | 88 | 12 |

100 mmHg for 8 hours while the solution was bubbled with dry air. Thus, the distilled liquid including toluene was separated.

Composition analysis of the tank liquid after reduced-pressure distillation was conducted using a high-performance liquid chromatograph equipped with a UV detector. As a result, the tank liquid was confirmed to include dipentaerythritol pentaacrylate and dipentaerythritol hexaacrylate as main components (hereinafter referred to as "DH-DPHA"). The calculated yield of the tank liquid regarded as a purified product was 80%. The hydroxyl valence of the obtained purified product was measured in the manner described above. As a result, it was 18 mg KOH/g. Table 3 shows the results.

5) Comparative Production Example 3 (Production of Polyfunctional Acrylate by a Dehydration Esterification Method)

Polyfunctional acrylate was produced in the manner described in Comparative Production Example 2 except that the following compounds listed in Table 3 were used as polyalcohols and a catalyst. Table 3 shows the results.

TABLE 3

| Comparative Production Example | Abbreviation | Polyalcohol | Catalyst | Purification yield (%) | Hydroxyl valence (mg KOH/g) |
|---|---|---|---|---|---|
| 2 | DH-DPHA | Dipentaerythritol | p-Toluenesulfonic acid | 80 | 18 |
| 3 | DH-PETTA | Pentaerythritol | p-Toluenesulfonic acid | 72 | 18 |

6) Production Example 4 (Production of Alkali-Soluble Resin as Component (H))

Into a separable flask equipped with a stirrer, a thermometer, a reflux cooling tube, a drip funnel, and a nitrogen introducing tube, 52.9 parts of methacrylic acid methyl, 22.5 parts of benzyl methacrylate, 24.6 parts of acrylic acid, 230 parts of propylene glycol monomethylether acetate ("PGM-AC" manufactured by Kuraray Co., Ltd., hereinafter referred to as "PGM-AC"), and 11.0 parts of dimethyl 2,2'-azobis(2-methylpropionate) were introduced in such proportions and uniformly dissolved. Then, the solution was stirred under a nitrogen stream at 85° C. for 4.5 hours, and the reaction was allowed to take place at 110° C. for 1 hour.

(2) To the solution obtained in (1) above, 26.25 parts of glycidyl methacrylate, 22.5 parts of PGM-Ac, and 0.2 parts of hydroquinone monomethylether were introduced in such proportions and then stirred at 100° C. for 5 hours. Thus, a reaction solution B (solid content concentration of 31.5%) including an alkali-soluble resin (h1) was obtained.

The weight-average molecular weight (Mw) of this alkali-soluble resin (h1) was 7,400 and the acid value thereof was 76 mg KOH/g (solid content conversion).

2. Examples and Comparative Examples

1) Method of Evaluating Purified Product

The purified products obtained in the Production Examples and Comparative Production Examples described above were evaluated in terms of high-molecular-weight body GPC area percent (%), viscosity, resistance to emulsification, metal ion concentration and preservation stability in accordance with the following methods. Table 4 shows the results.

(1) GPC area percent (%) of High-Molecular-Weight body

The area percent (%) of a high-molecular-weight body was calculated for the obtained purified products by GPC measurement under the following conditions.

GPC measurement conditions

Device: GPC manufactured by Waters; system name: 1515 2414 717P RI

Detector: RI detector

Column: Guard column: SHODEX KFG (8 μm, 4.6×10 mm) manufactured by Showa Denko K.K.; two types of main columns: STYRAGEL HR 4E THF (7.8×300 mm)+STYRAGEL HR 1THF (7.8×300 mm) manufactured by Waters Column temperature: 40° C.

Eluent composition: THF (including 0.03% of sulfur as an internal standard); flow rate: 0.75 mL/minute Method of calculating the area percent (%) of a high-molecular-weight body The area percent (%) was calculated based on the GPC measurement results according to the following Formula (1).

$$\text{Area percent of high-molecular-weight body}(\%) = [(R-I-L)/R] \times 100 \quad (1)$$

Symbols and terms used in Formula (1) are the same as defined above.

(2) Viscosity

Viscosity of the obtained purified product was measured by a type E viscometer (25° C. or 50° C.).

(3) Resistance to Emulsification

The obtained purified product in an amount of 3 g was dissolved in 6 g of xylene, 9 g of distilled layer was introduced into a glass test tube (18 mdi, hard glass), and the tube was capped. The tube was shaken vertically 10 times for emulsification and then allowed to stand still. The period of time required for complete separation between the aqueous layer and the organic layer was measured. The upper layer and the lower layer were evaluated in terms of transparency in accordance with the following criteria. There is a correlation between water separability and resistance to emulsification. A higher level of water separability indicates a higher level of resistance to emulsification in a case in which the purified product is used for ink.

AA: Transparent
A: Slightly turbid
B: Turbid
C: Emulsified (4) Metal Ion Concentration The metal ion concentration in a product is measured by a calibration curve method in accordance with JIS K 0121-1993 (General rules for atomic absorption spectrometry). To 1 g of a sample, 9 mL of methanol is added. Measurement is conducted by a frame method.

There is a correlation between the metal ion concentration in polyfunctional acrylate and electric properties. By reducing the metal ion concentration in polyfunctional acrylate, metal ion migration can be prevented when forming a device using polyfunctional acrylate.

(5) Preservation Stability Test

A glass test tube (18 mdi, hard glass) containing 10 g of the obtained purified product was introduced into a heating block set to 120° C., followed by heating for 6 hours. Thereafter, the appearance was evaluated in accordance with the following criteria.

A: No thickened or gelled matter observed.
C: Thickened or gelled matter observed.

CARMINE 6B: Azo-based red colorant C.I. Pigment Red 57:1, Carmine 6B No. 6520 manufactured by Daido Chemical Corporation 3) Evaluation Method (1) Curing Ability The obtained compositions were each applied to a polyethylene terephthalate film (COSMOCHINE A4300 (thick-

TABLE 4

| | | High-molecular-weight body GPC area % | Viscosity (mPa · s) | Separation time | Resistance to emulsification | | Metal ion concentration (wt ppm) | Preservation stability |
| --- | --- | --- | --- | --- | --- | --- | --- | --- |
| | | | | | Upper layer transparency | Lower layer transparency | | |
| Production Example 1 | EX-DPHA1 | 17.3 | 1,670 (25° C.) | 5 min | A | AA | Na: 0.08 | A |
| Production Example 2 | EX-DPHA2 | 17.3 | 1,620 (25° C.) | 5 min | A | AA | Na: 0.04 | A |
| Production Example 3 | EX-PETTA1 | 10.2 | 46 (50° C.) | 30 sec | A | AA | Na: 0.06 | A |
| Comparative Production Example 1 | EX-PETTA2 | 11.0 | 49 (50° C.) | 30 sec | A | AA | Na: 0.08 | C |
| Comparative Production Example 2 | DH-DPHA | 36.6 | 7,000 (25° C.) | 10 min | B | A | Na: 4.3 | A |
| Comparative Production Example 3 | DH-PETTA | 35.9 | 76 (50° C.) | 4 min | A | AA | Na: 1.4 | A |

As is apparent from the results of Production Examples 1 to 3, as the high-molecular-weight body area of the component (A) of the invention was less than 30%, low viscosity and excellent resistance to emulsification were confirmed. In addition, as the metal ion concentration was very low, there was no concern of ion elution from a cured film.

Meanwhile, Comparative Production Example 1 is an example of polyfunctional acrylate obtained using, as the catalyst X, a phosphine-based compound via transesterification reaction. Although there were no problems of viscosity, emulsifiability, and ion elution, there was a problem of preservation stability.

In addition, the compositions in Comparative Production Examples 2 and 3 included a component produced by a conventional dehydration esterification method, and the high-molecular-weight body area was 30% or more. Therefore, viscosity was high and resistance to emulsification was poor. In addition, as the metal ion concentration was high, there was concern of reduction of electric properties due to ion elution from a cured film.

2) Production of Active energy beam-Curable Composition

The compounds listed in Tables 5 to 7 below were stirred and mixed in proportions shown in Tables 5 to 7, thereby producing active energy beam-curable compositions.

Evaluation was conducted as described below using the obtained compositions. Tables 5 to 7 show the results.

Figures in Tables 5 to 7 each represent the number of parts.

Abbreviations used in Tables 5 to 7 have the following meanings.

IRG907: 2-methyl-1-(4-methylthiophenyl)-2-morpholinopropane-1-one, IRGACURE 907 manufactured by BASF SE DAP-A: Diallyl phthalate prepolymer, DAISO DAP A manufactured by Daiso Co., Ltd.

ness of 100 μm) manufactured by Toyobo Co., Ltd.) by a bar coater such that the film thickness was adjusted to 5 μm.

The obtained test samples were each conveyed in the air atmosphere by a conveyor, which was adjusted to have irradiation energy of 100 mJ/cm$^2$ per pass within an ultraviolet range (UV-A) with a center wavelength of 365 nm at an intensity of 800 mW/cm$^2$, using a metal halide lamp manufactured by Eye Graphics Co., Ltd. such that the test samples were irradiated with ultraviolet ray.

In Examples 7 and 8 and Comparative Examples 7 and 8, a coating film was dried by a hot plate at 100° C. for 3 minutes, thereby forming a coating film with a dried coat thickness of 5 μm.

In the method of evaluating curing ability, the number of passes until surface tucks disappeared was calculated.

(2) Universal Hardness of Cured Film (Evaluation as Active Energy Beam-Curable Compositions for Coating Agents)

The compositions listed in Table 5 below were each applied by a bar coater to a 10-cm square glass substrate such that the film thickness was adjusted to 20 μm. The glass substrates were each conveyed in the air atmosphere by a conveyor, which was adjusted to have irradiation energy of 800 mJ/cm$^2$ per path within an ultraviolet range (UV-A) with a center wavelength of 365 nm at intensity of 500 mW/cm$^2$, using a high-pressure mercury lamp manufactured by Eye Graphics Co., Ltd. such that the glass substrates were irradiated with ultraviolet ray.

The obtained cured films hardness was evaluated in terms of hardness using a super microhardness tester (H-100C manufactured by Fischer Instruments K.K.) based on universal hardness obtained when measuring surface hardness under conditions, in which the maximum load of a Vickers indenter is 20 mN at room temperature.

(3) Resistance to Emulsification (Evaluation as Active Energy Beam-Curable Compositions for Ink)

The compositions listed in Table 6 were also evaluated by the method used for resistance to emulsification.

The evaluation results were similar to the results shown in Table 4.

(4) Alkali Developability (Evaluation as Active Energy Beam-Curable Compositions for Pattern Formation)

The compositions listed in Table 7 were each applied to a 10-cm square chrome-masked glass substrate using a spin coater. Each obtained coating film was dried by a hot plate at 100° C. for 3 minutes such that a coating film with a dried coat thickness of 5 μm was formed. The obtained coating films were each spray-developed with a 0.05% potassium hydroxide aqueous solution at a liquid temperature of 23° C., and the period of time required for complete dissolution was measured.

Examples 1 and 2 each including a component produced by a conventional dehydration esterification method. As the area percent (%) of the high-molecular-weight body of the component (A) was less than 30%, indicating that the cured film had excellent hardness.

Meanwhile, in the compositions of Comparative Examples 1 and 2 each including a component produced by a conventional dehydration esterification method, polyfunctional acrylate was a composition including a high-molecular-weight body at an area percent (%) of 30% or more. Therefore, the compositions were inferior to the compositions of the Examples in terms of cured film hardness.

As is apparent from the results in Examples 3 and 4, the composition of the invention showed curing ability comparable to that of the ink compositions of Comparative Examples 3 and 4 each including a component produced by a conventional dehydration esterification method.

TABLE 5

| | Composition (parts) | | | | Evaluation results | |
|---|---|---|---|---|---|---|
| | (A) | | (A') | | (B) | Curing ability | Universal hardness of |
| | EX-DPHA1 | EX-PETTA1 | DH-DPHA | DH-PETTA | IRG 907 | (No. of passes) | cured film (N/mm²) |
| Example 1 | 100 | | | | 5 | 1 | 390 |
| Example 2 | | 100 | | | 5 | 1 | 388 |
| Comparative Example 1 | | | 100 | | 5 | 1 | 352 |
| Comparative Example 2 | | | | 100 | 5 | 1 | 351 |

TABLE 6

| | Composition (parts) | | | | | | | Evaluation results |
|---|---|---|---|---|---|---|---|---|
| | (A) | | (A') | | (B) | | (G) | Curing ability |
| | EX-DPHA1 | EX-PETTA1 | DH-DPHA | DH-PETTA | IRG 907 | (F) DAP-A | CARMINE 6B | (No. of passes) |
| Example 3 | 65 | | | | 5 | 10 | 20 | 1 |
| Example 4 | | 65 | | | 5 | 10 | 20 | 1 |
| Comparative Example 3 | | | 65 | | 5 | 10 | 20 | 1 |
| Comparative Example 4 | | | | 65 | 5 | 10 | 20 | 1 |

TABLE 7

| | Composition (parts) | | | | | | | Evaluation results | |
|---|---|---|---|---|---|---|---|---|---|
| | (A) | | (A') | | (B) | | (E) | Curing ability | Alkali |
| | EX-DPHA1 | EX-PETTA1 | DH-DPHA | DH-PETTA | IRG 907 | (H) h1 | PGM-Ac 109 | (No. of passes) | developability (sec) |
| Example 5 | 50 | | | | 5 | 50 | 109 | 1 | 20 |
| Example 6 | | 50 | | | 5 | 50 | 109 | 1 | 15 |
| Comparative Example 5 | | | 50 | | 5 | 50 | 109 | 1 | 30 |
| Comparative Example 6 | | | | 50 | 5 | 50 | 109 | 1 | 25 |

As is apparent from the results in Examples 1 and 2, the composition of the invention had curing ability at a level comparable to the levels of the compositions of Comparative In addition, as described above, since the component (A) had excellent resistance to emulsification, the ink composition including the component (A) also had excellent resistance to emulsification, indicating that the component (A) is favorable as an ink composition. Meanwhile, the material polyfunctional acrylate had insufficient resistance to emulsification for the ink compositions of Comparative Examples 3 and 4, compared with the corresponding component (A). Therefore, the ink compositions also had insufficient resistance to emulsification.

As is apparent from the results in Examples 5 and 6, the composition of the invention showed curing ability comparable to that of the pattern formation compositions of Comparative Examples 5 and 6 each including a component produced by a conventional dehydration esterification method, and the composition of the invention had alkali developability more excellent than that of the compositions of Comparative Examples 5 and 6. Further, as described above, since the component (A) had a low metal ion concentration, it was favorable as a pattern formation composition free from concern of reduction in electric properties.

INDUSTRIAL APPLICABILITY

The composition of the invention can be used for various purposes including coating such as hard coating, ink for offset or ink-jet printing, photosensitive lithographic printing plates, resists such as color resists, and so on.

What is claimed is:

1. A method of producing a curable composition, which comprises a step of producing a mixture (A) of a compound having two or more (meth)acryloyl groups that is obtained by conducting a transesterification reaction of a polyalcohol and a compound having one (meth)acryloyl group under the presence of the following catalysts X and Y:

catalyst X: a compound that is at least one selected from the group consisting of cyclic tertiary amine having an azabicyclo structure or a salt or complex thereof, amidine or a salt or complex thereof, and a compound having a pyridine ring or a salt or complex thereof; and catalyst Y: a compound including zinc.

2. The method of producing a curable composition according to claim 1, wherein the polyalcohol is a polyalcohol having three or more alcoholic hydroxyl groups.

3. The method of producing a curable composition according to claim 2, wherein the polyalcohol is dipentaerythritol or pentaerythritol.

4. The method of producing a curable composition according to claim 1, wherein the compound having one (meth)acryloyl group is alkoxyalkyl(meth)acrylate.

5. The method of producing a curable composition according to claim 1, wherein the catalyst Y is organic acid zinc and/or zinc diketone enolate.

6. The method of producing a curable composition according to claim 1, which includes a step of mixing in a photopolymerization initiator (B) after production of (A) as a component.

7. The method of producing a curable composition according to claim 1, wherein (A) is a component having a hydroxyl valence of not more than 60 mg KOH/g.

* * * * *